(12) United States Patent
Wu et al.

(10) Patent No.: US 12,349,880 B2
(45) Date of Patent: Jul. 8, 2025

(54) ORAL FIXATION APPARATUS

(71) Applicant: PAPRICA LAB. CO., LTD., Seoul (KR)

(72) Inventors: Hong Gyun Wu, Seoul (KR); Jong Min Park, Seoul (KR); Jung In Kim, Seoul (KR); Chang Heon Choi, Gyeonggi-do (KR); Jae Man Son, Seoul (KR); Ji Seong Kim, Seoul (KR)

(73) Assignee: PAPRICA LAB. CO., LTD., Seoul (KR)

( * ) Notice: Subject to any disclaimer, the term of this patent is extended or adjusted under 35 U.S.C. 154(b) by 779 days.

(21) Appl. No.: 17/629,551

(22) PCT Filed: Jun. 4, 2020

(86) PCT No.: PCT/KR2020/007243
§ 371 (c)(1),
(2) Date: Jan. 24, 2022

(87) PCT Pub. No.: WO2021/015410
PCT Pub. Date: Jan. 28, 2021

(65) Prior Publication Data
US 2022/0265253 A1     Aug. 25, 2022

(30) Foreign Application Priority Data

Jul. 25, 2019    (KR) .................. 10-2019-0089944
Jan. 31, 2020    (KR) .................. 10-2020-0011459

(51) Int. Cl.
*A61B 13/00*     (2006.01)
*A61B 5/00*     (2006.01)

(52) U.S. Cl.
CPC ............... *A61B 13/00* (2013.01); *A61B 5/70* (2013.01)

(58) Field of Classification Search
CPC .. A61B 13/00; A61B 5/70; A61B 1/00; A61B 1/24; A61B 1/32; A61N 5/10;
(Continued)

(56) References Cited

U.S. PATENT DOCUMENTS 8,833,374 B2 *   9/2014   Fallon .................... A61F 5/566
                                                   433/68
2014/0190489 A1    7/2014   Chen et al.

FOREIGN PATENT DOCUMENTS

DE    202010000010 U1 *   6/2010 ............. B66F 15/00
JP           2617881 B2 *   6/1997
(Continued)

OTHER PUBLICATIONS

KR 101859275 machine translation (Year: 2018).*
(Continued)

*Primary Examiner* — Caitlin A Carreiro
(74) *Attorney, Agent, or Firm* — The PL Law Group, PLLC

(57) ABSTRACT

An oral fixation apparatus according to an embodiment of the present disclosure includes a mouthpiece provided to be mounted in a mouth, and a pressing unit configured to move relative to the mouthpiece, wherein the pressing unit is configured to press a tongue in the mouth to any one side in the mouth. Through this configuration, the oral fixation apparatus may maintain the same intraoral state. The oral fixation apparatus may be stably mounted inside the mouth, such that radiation therapy may be effectively and stably performed.

17 Claims, 30 Drawing Sheets

(58) Field of Classification Search
CPC .......... A61C 19/00; A61C 19/06; A61C 5/00; A61C 5/90; A61C 7/08; A61F 5/56; A61F 5/566; A63B 71/085
USPC ............... 128/845, 860, 861; 433/6, 93, 140
See application file for complete search history.

(56) References Cited

FOREIGN PATENT DOCUMENTS

| | | | |
|---|---|---|---|
| KR | 100686607 B1 | * | 2/2007 |
| KR | 10-1668178 B1 | | 10/2016 |
| KR | 101859275 B1 | * | 5/2018 |

OTHER PUBLICATIONS

KR 100686607 machine translation (Year: 2007).*
DE 202010000010 U1 machine translation (Year: 2010).*
JP 2617881 B2 (Year: 1997).*
International Search Report for PCT/KR2020/007243 mailed on Sep. 18, 2020.

* cited by examiner

ORAL FIXATION APPARATUS

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2020/007243, filed Jun. 4, 2020, which claims priority to the benefit of Korean Patent Application Nos. 10-2019-0089944 filed on Jul. 25, 2019 and 10-2020-0011459 filed in the Korean Intellectual Property Office on Jan. 31, 2020, the entire contents of which are incorporated herein by reference.

BACKGROUND

1. Technical Field

The present invention relates to an oral fixation apparatus.

2. Background Art

Radiation therapy is one of three major methods for treating cancer, along with surgery and chemotherapy as a method of clinical medicine for treating a patient by using radiation having a very short wavelength and high energy. The radiation therapy is mainly intended to treat malignant tumors called cancer, but also to treat benign tumors and some benign diseases.

When performing radiation therapy, a treatment is executed by irradiating a target site with radiation. However, in actual radiation therapy, a site adjacent to the target site may be irradiated with radiation. In particular, when performing radiation therapy on a target site in the mouth, a tongue or oral mucosa, which are healthy tissues, may also be irradiated with radiation, thereby causing damage to the tongue or oral mucosa. If radiation is irradiated farther than the planned point due to a change in a body type of the patient or uncertainty arising from a therapeutic apparatus, the tongue or surrounding normal organs may be unnecessarily irradiated with radiation, thereby causing damage to the corresponding site.

In addition, since radiation therapy is composed of fractionated radiation therapy performed several times, it is important to maintain the same oral state. However, since the inside of the mouth is composed of flexible tissue, there is a problem that the distribution of radiation dose delivered to the patient is different from the plan.

Due to these problems, upon repeated radiation therapy, a device capable of maintaining the same intraoral state is required.

SUMMARY

One object of the present invention is to provide an oral fixation apparatus for stably fixing a mouth.

In addition, another object of the present invention is to provide an oral fixation apparatus capable of fixing a position of a tongue.

Further, another object of the present invention is to provide an oral fixation apparatus capable of maintaining the same position at all times even when repeatedly mounting the device.

To achieve the above objects, according to an aspect of the present invention, there is provided an oral fixation apparatus including: a mouthpiece mounted in a mouth; and a pressing unit movably coupled to the mouthpiece, wherein the pressing unit is configured to press a tongue in the mouth.

The mouthpiece may include: a first body corresponding to upper teeth and a second body corresponding to lower teeth; and a shape holding part disposed on an upper portion of the first body and a lower portion of the second body, respectively, wherein a reference groove is formed while the upper and lower teeth are inserted therein.

The shape holding part may be configured to be cured in a state in which the reference groove is formed.

The shape holding part may include: inclined surfaces slantly formed on a surface thereof; and a seat surface formed on the surface of the shape holding part, wherein the seat surface and the inclined surfaces form an insertion space which is concave on the surface of the shape holding part, wherein the reference groove is disposed on the seat surface.

The mouthpiece may further include: first and second guide bodies disposed between the shape holding part and the first and second bodies, wherein the first and second guide bodies are detachably coupled to the first and second bodies together with the shape holding part mounted on one surface thereof.

The pressing unit may move relative to the mouthpiece between the first and second bodies.

The pressing unit may move between a first position and a second position in which the pressing unit is rotated in a yaw direction from the first position, and the oral fixation apparatus may further include: a rotation guide forming a rotation axis of the pressing unit in the yaw direction, wherein the rotation guide maintains the pressing unit located in either the first position or the second position.

The oral fixation apparatus may further include a mounting holder which has a mounting hole in which the pressing unit is mounted, and rotates on the rotation axis relative to the rotation guide together with the pressing unit, wherein the mounting holder and the rotating guide maintain the pressing unit located in either the first position or the second position.

The mounting holder may include tooth-shaped engaging gears formed on an outer surface thereof, and the rotation guide may include gear grooves formed in an inner surface thereof and configured to be engaged with the engaging gears so as to limit a rotation of the mounting holder.

The engaging gear may include: an adjustment gear composed of teeth formed with a longer length than a protruding length of adjacent teeth, and the gear groove may include: a plurality of adjustment grooves formed with a deeper depth than the depth of adjacent grooves, wherein plurality of adjustment grooves are configured so that the adjustment gear is inserted into any one adjustment groove of the plurality of adjustment grooves.

A position of the pressing unit may be changed between a first state and a second state in which the pressing unit is rotated in a roll direction from the first state, and the position of the pressing unit may be changed by separating and mounting the pressing unit from and in the mounting holder.

The mounting hole may have a cross section formed in a polygonal shape corresponding to an outer surface of the pressing unit so as to limit a rotation of the pressing unit in the roll direction with being mounted in the mounting hole.

The mouthpiece may include: a first body corresponding to upper teeth and a second body corresponding to lower teeth, and the rotation guide may include: a first guide part disposed in the first body to guide a rotation of the mounting holder on one side; and a second guide part disposed in the second body to guide the rotation of the mounting holder on the other side.

The first and second bodies may be symmetrically arranged, and any one guide part of the first and second guide parts is disposed to protrude forward from the first and second bodies so as to have an asymmetric structure relative to the symmetric first and second bodies.

The pressing unit may include: a handle part; and a pressing head located at an end of the handle part, and configured to be in contact with the tongue so as to press the tongue by a rotation in the yaw direction.

The handle part may be configured to be exposed to an outside of the mouth when the oral fixation apparatus is mounted in the mouth.

The oral fixation apparatus may further include a length adjustment part configured to adjust a length in which the pressing head is inserted into the mouth, wherein the length adjustment part has a plurality of adjustment grooves into which an insert protrusion located on the mouthpiece is selectively inserted, which are paced apart from each other in a longitudinal direction of the handle part.

According to one embodiment of the present invention, the oral fixation apparatus may be stably mounted inside the mouth, such that radiation therapy may be effectively and stably performed.

In addition, according to one embodiment of the present invention, the oral fixation apparatus may maintain the same posture by taking an impression through user's teeth even upon repeated radiation therapy.

Further, according to one embodiment of the present invention, through the pressing unit which allows the user to adjust the length and rotation angle of the oral fixation apparatus, individual customized fine adjustment is possible, and the tongue may be located at the same position even upon the repeated radiation therapy.

DETAILED DESCRIPTION

Figure 1:
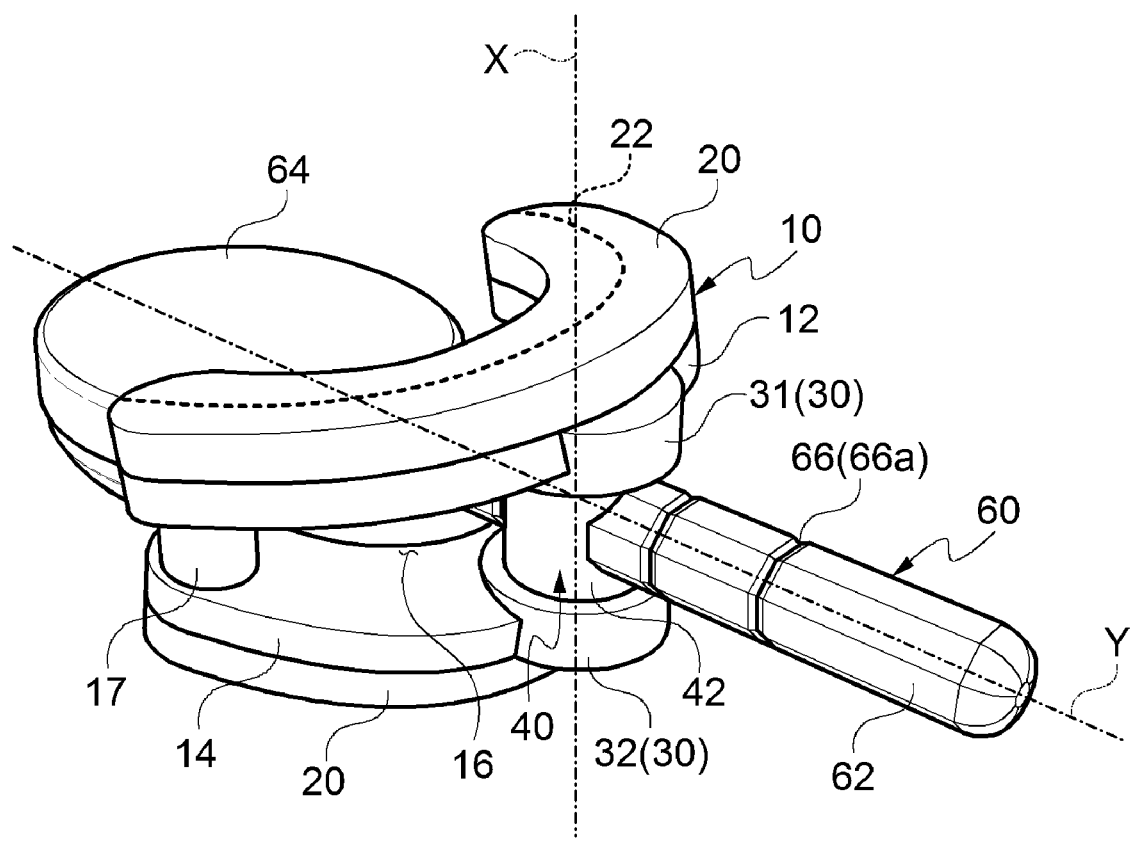
FIG. 1 is a perspective view illustrating an oral fixation apparatus according to an embodiment of the present invention.

Configurations illustrated in the embodiments and drawings of the present disclosure are only preferred examples of the invention, and diverse modifications capable of replacing the embodiments and drawings of the present disclosure may be possible at a time of filing the present application.

Further, the same reference numerals or symbols in the drawings of the present disclosure will represent parts or components having substantially the same functions.

In addition, the terminology used herein is for the purpose of describing particular embodiments only and is not intended to limit the present invention thereto. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Further, the terms including numerals such as "first," "second," etc. in the present disclosure may be used to describe different components, but such components are not limited thereto. These terms are used only to distinguish one component from other components. For example, a first component may also be named a second component without departing from the scope of the present invention. Likewise, the second component may also be named the first component. The term "and/or" may include a coupling of a plurality of related items and/or any one among the plurality of related items.

In addition, the terms such as a "part," "device," "block," "member," "module," and the like may refer to a unit to execute at least one function or operation. For example, the terms may refer to at least one hardware such as a field-programmable gate array (FPGA) or an application specific integrated circuit (ASIC), at least one operating process performed by at least one software stored in a memory or processor.

Hereinafter, preferred embodiments of the present invention will be described in detail with reference to the accompanying drawings.

Figure 2:
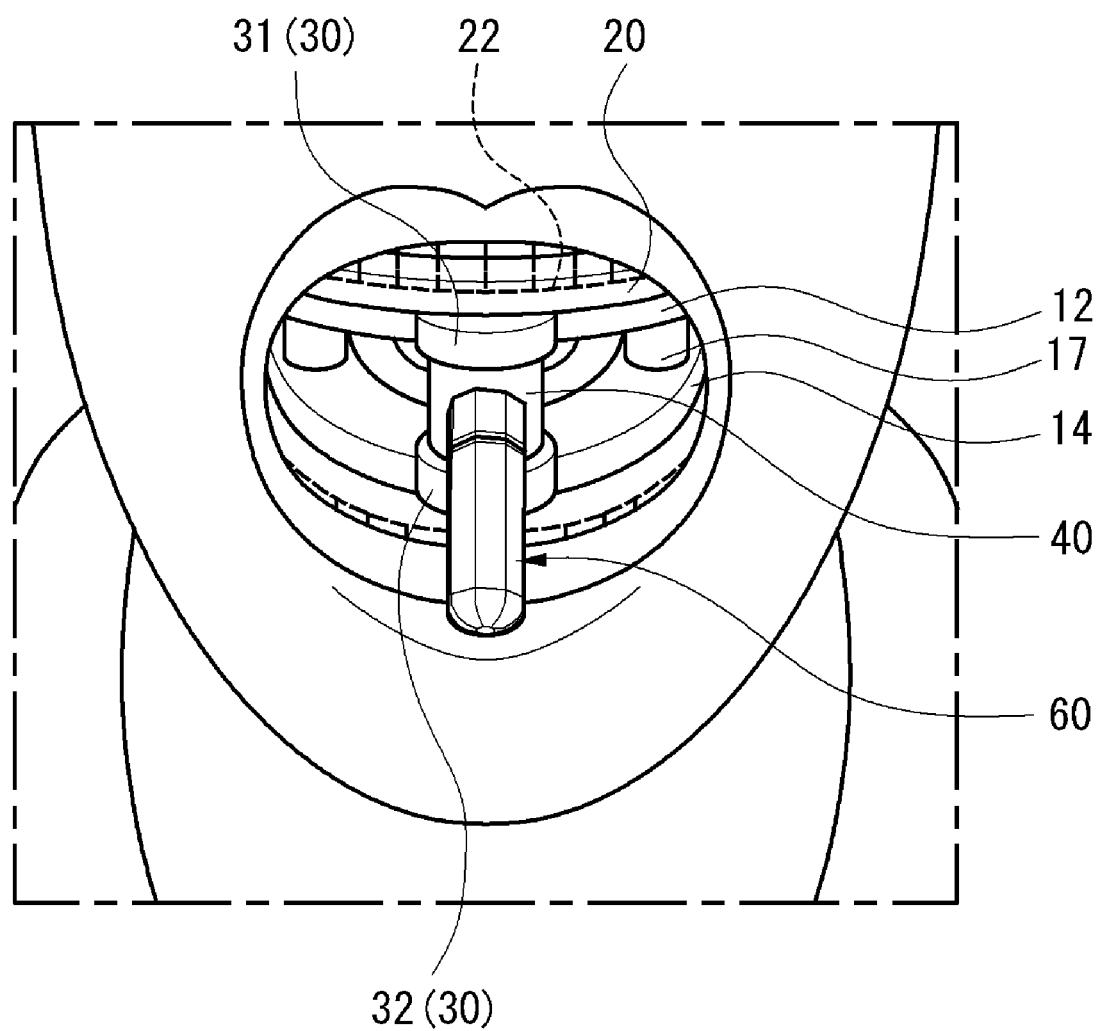
FIG. 2 is a view illustrating a state in which the oral fixation apparatus according to an embodiment of the present invention is mounted in a mouth.

FIG. 1 is a perspective view illustrating an oral fixation apparatus according to an embodiment of the present invention, and FIG. 2 is a view illustrating a state in which the oral fixation apparatus according to an embodiment of the present invention is mounted in a mouth.

An oral fixation apparatus 1 is configured to be inserted into a mouth. The oral fixation apparatus 1 may maintain the same intraoral state upon repeated radiation therapy.

The oral fixation apparatus 1 may include a mouthpiece 10 and a pressing unit 60.

The mouthpiece 10 is provided to be inserted or mounted in the mouth. The mouthpiece 10 may be fixed by teeth inserted therein in the mouth. The mouthpiece 10 may be formed in a U shape corresponding to an arrangement of the teeth. The mouthpiece 10 may serve as a reference for rotation or movement of an operation of the pressing unit 60 to be described below.

The mouthpiece 10 may include a first body 12 corresponding to upper teeth and a second body 14 corresponding to lower teeth. The first and second bodies 12 and 14 are provided to be spaced apart from each other by a predetermined angle, thereby allowing a user to maintain a state of naturally biting the oral fixation apparatus 1. The first and second bodies 12 and 14 may be formed longitudinally in a direction of the row of teeth. The first and second bodies 12 and 14 may be configured to have the same shape as each other. Since the first and second bodies 12 and 14 correspond to the upper teeth and lower teeth, respectively, they may be configured to have different sizes.

The mouthpiece 10 may include shape holding parts 20 for taking an impression. When a subject to be measured bites the mouthpiece 10 of the oral fixation apparatus 1 as shown in FIG. 2, the shape holding parts 20 may have a reference groove 22 corresponding to the teeth of the subject, which is formed when the teeth is inserted into the bodies. The reference groove 22 may be formed in a shape corresponding to the row of teeth of the subject. The shape holding part 20 may be cured in a state in which the reference groove 22 is formed. The cured shape holding part 20 allows the oral fixation apparatus 1 to be located at the same position and arrangement in the user's mouth upon repeated radiation therapy. That is, by inserting the teeth into the cured and preformed reference groove 22, the oral fixation apparatus 1 may be configured to be located at the same position and arrangement in the mouth. Thereby, the same reference position in a roll direction and a reference position in a yaw direction of the pressing unit 60, which will be described below, may be set. The reference groove 22 may be molded to fit the oral structure or the row of teeth of a patient considering a biting pressure or the like applied to the shape holding part 20 by the subject. FIG. 1 illustrates an example in which the reference groove 22 is formed in an arc shape as shown by a dotted line in a longitudinal direction of the shape holding part 20. However, it is not limited thereto, and the reference groove 22 may be formed in a concave groove shape corresponding to the row of teeth of the subject.

A material of the shape holding part 20 is not limited, and any material may be used so long as it can sufficiently maintain the deformed state of the oral fixation apparatus by an external force. For example, the shape holding part 20 may include ethylene vinyl acetate (EVA).

The shape holding parts 20 may be disposed on an upper surface of the first body 12 and a lower surface of the second body 14, respectively. That is, the shape holding parts 20 may be disposed on the upper surface of the first body 12 corresponding to the upper teeth, and may be disposed on the lower surface of the second body 14 corresponding to the lower teeth. The reference grooves 22 may be formed in a shape corresponding to the rows of the upper teeth and the lower teeth, respectively.

The shape holding parts 20 may be configured to cover the entire upper surface of the first body 12 and the entire lower surface of the second body 14. Through this configuration, forces transmitted from the upper and lower teeth to the shape holding parts 20 are uniformly transmitted to the first and second bodies 12 and 14, such that the oral fixation apparatus 1 may stably support the inside of the mouth.

The pressing unit 60 may be provided to move relative to the mouthpiece 10. The pressing unit 60 may be configured so that a portion thereof is inserted into the mouth to press the tongue in any one direction of several directions inside the mouth. The pressing unit 60 may rotate relative to the mouthpiece 10 in the roll direction, rotate in the yaw direction, and move in a forward and backward direction. A reference in the mouth is set through the mouthpiece 10, and after the reference has been set, it is possible to maintain the same intraoral state for each subject through fine adjustment of the pressing unit 60. The mouths, which are formed differently for a plurality of subjects, may be applied differently through the oral fixation apparatus, and the individual subject may repeatedly have the same intraoral environment. The pressing unit 60 will be described in detail below.

The oral fixation apparatus 1 may include a rotation guide 30. The rotation guide 30 may be one component of the mouthpiece 10. The rotation guide 30 is provided to guide a rotational operation of the pressing unit 60. That is, the rotation guide 30 may form a rotation axis of the pressing unit 60 in the yaw direction. The rotation guide 30 may be provided in the first and second bodies 12 and 14 of the mouthpiece 10. The rotation guide 30 may include a first guide part 31 provided in the first body 12 and a second guide part 32 provided in the second body 14. The rotation guide 30 will be described in detail below.

The oral fixation apparatus 1 may include a mounting holder 40. The mounting holder 40 may be provided rotatable relative to the rotation guide 30. The mounting holder 40 may be provided to rotate about the rotation axis formed by the rotation guide 30 in the yaw direction together with the pressing unit 60. The mounting holder 40 may be configured to maintain a position in which the pressing unit 60 has been rotated in the yaw direction together with the rotation guide 30. The mounting holder 40 may be one component of the mouthpiece 10 together with the rotation guide 30. The mounting holder 40 will be described in detail below.

Figure 3:
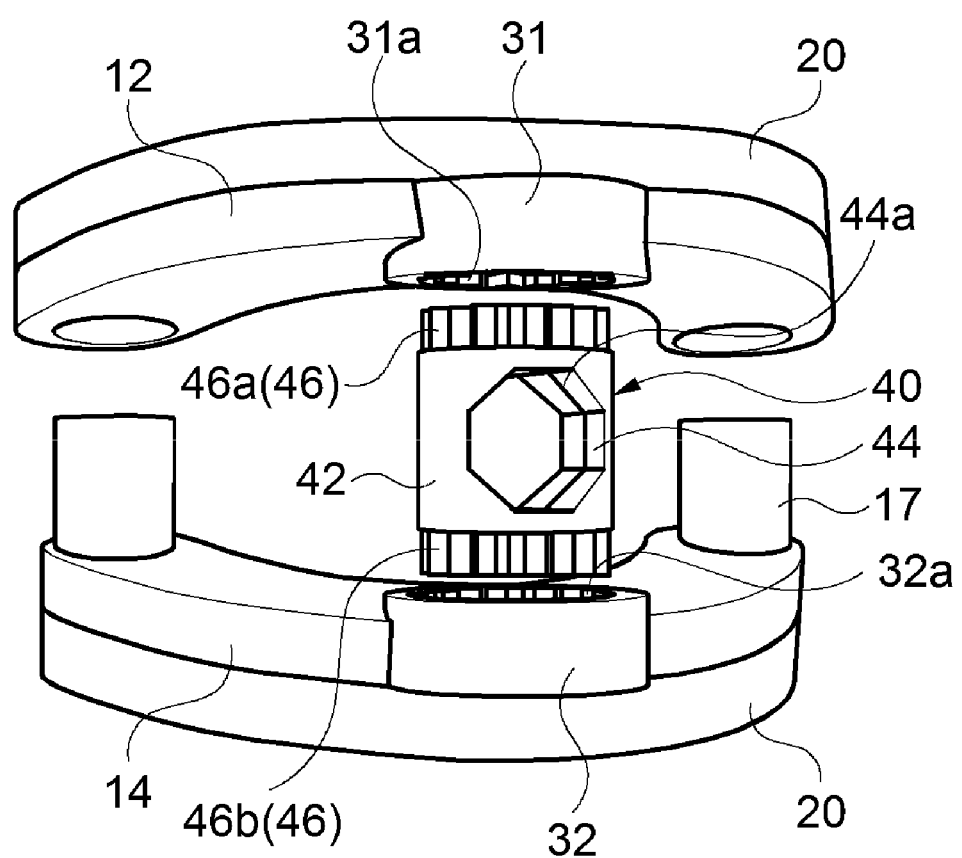
FIG. 3 is an exploded perspective view illustrating a mouthpiece and a mounting holder of the oral fixation apparatus according to an embodiment of the present invention.
Figure 4:
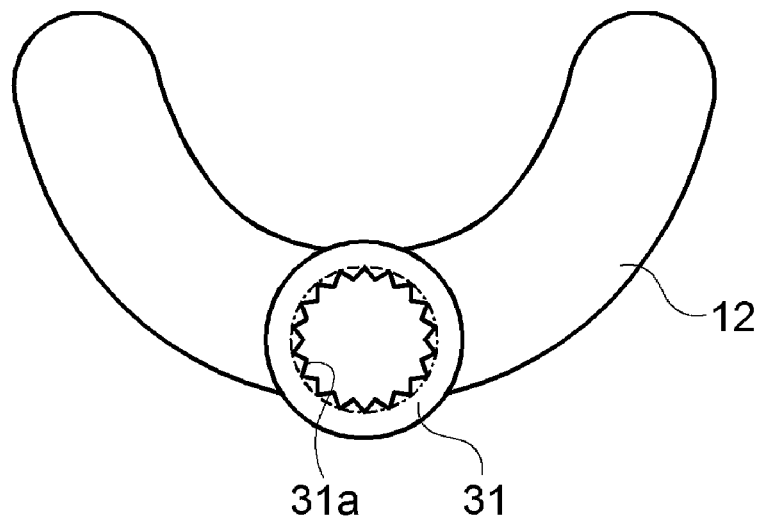
FIGS. 4 and 5 are plan views of the mouthpiece of the oral fixation apparatus according to an embodiment of the present invention.
Figure 5:
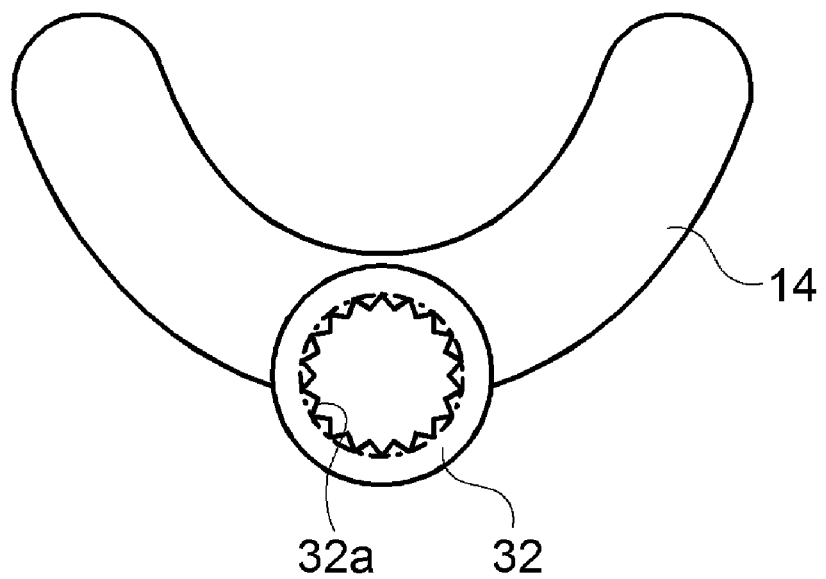

FIG. 3 is an exploded perspective view illustrating the mouthpiece and the mounting holder of the oral fixation apparatus according to an embodiment of the present invention, and FIGS. 4 and 5 are plan views of the mouthpiece of the oral fixation apparatus according to an embodiment of the present invention.

The first and second bodies 12 and 14 of the mouthpiece 10 are configured so as to maintain a state in which they are spaced apart from each other at a predetermined angle. That is, the first and second bodies 12 and 14 may be disposed so that they are spaced apart from each other to form an open space 16 (see FIG. 1) therebetween. The pressing unit 60 may be located inside the mouth through the open space 16 shown in FIG. 1. The pressing unit 60 may move relative with respect to the mouthpiece 10 between the first and second bodies 12 and 14.

The mouthpiece 10 may include connection parts 17 provided at rear portions of the first and second bodies 12 and 14 to support the first and second bodies 12 and 14. The connection part 17 may be configured to connect the first and second bodies 12 and 14 while maintaining the state in which they are spaced apart from each other at a predetermined angle on a rear side of the first and second bodies 12 and 14, that is, at the side portions of the back teeth.

The mounting holder 40 may be located on a front side of the first and second bodies 12 and 14, that is, corresponding to side portions of the front teeth. The mounting holder 40 is formed in a substantially column shape, and is configured to be connected to the first and second bodies 12 and 14 while maintaining the state in which they are spaced apart from each other at a predetermined angle together with connection parts 17.

The mounting holder 40 may be formed to be longer than the connection part 17. Due to a difference in the length between the mounting holder 40 and the connection part 17, front portions of the mouthpiece 10 may be configured to be spaced apart from each other more than rear portions of the mouthpiece 10. Thereby, the oral fixation apparatus 1 may be inserted into the naturally opened mouth to maintain an open state of the mouth.

The mounting holder 40 may include a holder body 42 forming a body thereof, a mounting hole 44, and a mounting part 46.

The mounting hole 44 may be formed in the holder body 42. The mounting hole 44 may be formed to pass through the holder body 42. The pressing unit 60 is inserted into the mounting hole 44 and fixed thereto. The mounting hole 44 may have a cross-section formed in a polygonal shape. Through this configuration, while the pressing unit 60 having an outer surface formed in a polygonal shape corresponding to the mounting hole 44 is inserted into the mounting hole 44, it is possible to prevent the pressing unit 60 from being rotated in the roll direction about the longitudinal direction thereof as an axis.

The mounting part 46 is provided to be guided in a rotation thereof by the rotation guide 30 or to be maintained in the rotated state. The mounting part 46 may include a first mounting part 46a provided on one side of the mounting holder 40 and a second mounting part 46b provided on the other side of the mounting holder 40. When the mounting holder 40 is installed on the rotation guide 30, the first and second mounting parts 46a and 46b may be located inside the first and second guide parts 31 and 32, respectively. Rotations of the first and second mounting parts 46a and 46b may be guided by the first and second guide parts 31 and 32, respectively.

The first and second mounting parts 46a and 46b are formed in a substantially cylindrical shape, and the first and second guide parts 31 and 32 are formed in a substantially cylindrical groove shape. Therefore, the first and second mounting parts 46a and 46b may be inserted into the first and second guide parts 31 and 32, respectively. The first and second mounting parts 46a and 46b are inserted into the first and second guide parts 31 and 32, such that the mounting holder 40 may be configured to be rotated relative to the rotation guide 30. Through this configuration, the pressing unit 60 mounted in the mounting holder 40 may be rotatably installed in the yaw direction relative to the mouthpiece 10. Specifically, when the longitudinal direction of the mounting holder 40 is referred to as an X-axis direction, the pressing unit 60 mounted in the mounting holder 40 is provided to rotate about the X-axis on a plane perpendicular to the X-axis.

Outer circumferential surfaces of the first and second mounting parts 46a and 46b and inner circumferential surfaces of the first and second guide parts 31 and 32 are formed in a toothed gear shape, such that the position of the rotated mounting holder 40 may be maintained. That is, engaging gears 48a and 48b formed on the outer circumferential surfaces of the first and second mounting parts 46a and 46b, and gear grooves 31a and 32a formed on the inner circumferential surfaces of the first and second guide parts 31 and 32 may be located alternately in a circumferential direction. The engaging gears 48a and 48b and the gear grooves 31a and 32a may be formed in a toothed shape, and may be configured to mesh with each other.

When rotating the pressing unit 60, the engaging gears 48a and 48b may move on the gear grooves 31a and 32a by an external force. When the rotation operation of the pressing unit 60 is finished, rotation of the teeth of the engaging gears 48a and 48b is limited by the teeth of the gear grooves 31a and 32a. Thereby, the rotated state of the mounting holder 40 relative to the rotation guide 30 may be maintained.

Since a plurality of engaging gears 48a and 48b and a plurality of gear grooves 31a and 32a are provided in the circumferential direction, the pressing unit 60 may be finely rotated in the yaw direction and may be maintained in the rotated state relative to the mouthpiece 10.

The first and second guide parts 31 and 32 may be disposed at different positions relative to the first and second bodies 12 and 14 of the mouthpiece 10. Specifically, the second guide part 32 disposed in the second body 14 may be located to protrude forward relative to the first body 12 from the first guide part 31 disposed in the first body 12. As shown in FIGS. 4 and 5, a protrusion amount of the second guide part 32 from the second body 14 may be greater than the protrusion amount of the first guide part 31 from the first body 12.

That is, the first and second guide parts 31 and 32 may have an asymmetric structure relative to the first and second bodies 12 and 14. Through this asymmetric structure, the pressing head 64 of the pressing unit 60 may face downward more than in the case of a symmetric structure. When the pressing head 64 faces a lower portion of the mouth, it is possible to press a lower side portion of the tongue, thereby stably pressing the tongue to any one side in the mouth.

Figure 6:
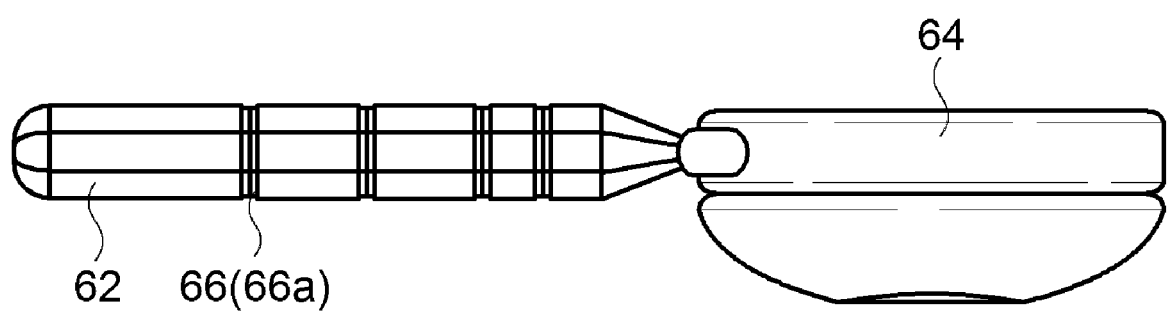
FIG. 6 is a rear view illustrating a pressing unit of the oral fixation apparatus according to an embodiment of the present invention.
Figure 7:
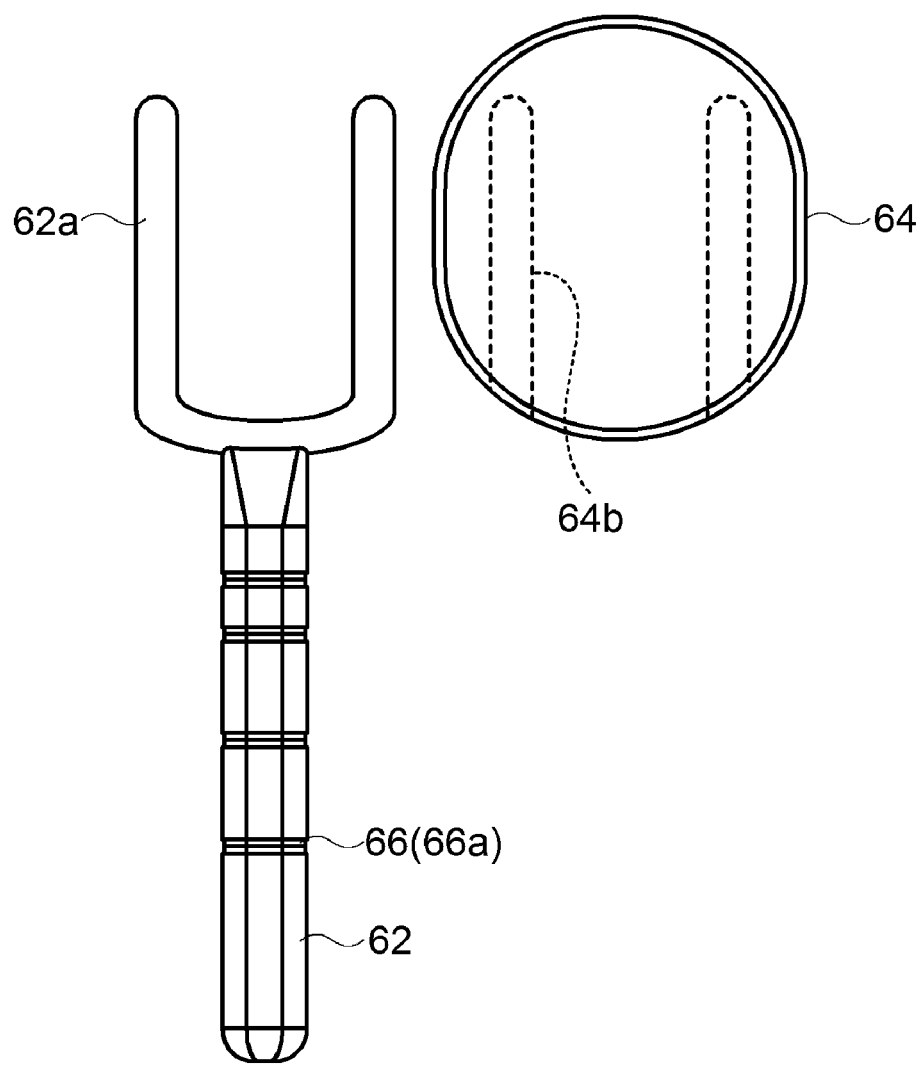
FIG. 7 is an exploded view of the pressing unit of the oral fixation apparatus according to an embodiment of the present invention.

FIG. 6 is a rear view illustrating a pressing unit of the oral fixation apparatus according to an embodiment of the present invention, and FIG. 7 is an exploded view of the pressing unit of the oral fixation apparatus according to an embodiment of the present invention.

The pressing unit 60 may press the tongue so as to bias the tongue to any one side in the mouth through a manipulation. When the oral fixation apparatus 1 is mounted in the mouth, the pressing unit 60 may be configured so that at least a part thereof is exposed to an outside of the mouth.

The pressing unit 60 may include a handle part 62 and a pressing head 64.

The handle part 62 is configured to be gripped by a hand, and is provided to be rotated in the yaw direction of the pressing unit 60 due to an external force applied thereto, as described above. The handle part 62 is provided to be exposed to the outside of the mouth when the oral fixation apparatus 1 is mounted in the mouth. Through this configuration, it is possible to control the intraoral state by manipulating the handle part 62.

The handle part 62 may have an outer surface formed in a polygonal shape corresponding to the mounting hole 44 of the mounting holder 40. In the present embodiment, the configuration, in which the mounting hole 44 is formed in an octagonal shape, and the handle part 62 is also formed in an octagonal shape corresponding thereto, has been described as an example. However, it is not limited thereto, and the mounting hole 44 and the handle part 62 may be formed in various polygonal shapes, or may be formed in a circular or oval shape.

It is possible to manipulate the handle part 62 so as to be the state rotated in the roll direction relative to the mounting holder 40. That is, it is possible to manipulate the handle part 62 so as to be the state rotated relative to the mounting holder 40 about a Y-axis, which is the longitudinal direction of the handle part 62. Since the handle part 62 and the mounting hole 44 are formed in the polygonal shapes corresponding to each other, the handle part 62 may be separated from the mounting holder 40, rotated in the roll direction, and then mounted in the mounting holder 40. Thereby, a direction in which the pressing head 64 faces may be adjusted through the above operation.

The pressing head 64 is provided to press a tongue in the mouth. The pressing head 64 may be connected to the handle part 62 and configured to rotate or move along with the rotation or movement of the handle part 62. In FIGS. 6 and 7, one surface of the pressing head 64 is formed in a substantially curved surface, and is provided in a substantially spatula shape. But, the shape thereof is not limited thereto, and any configuration may be used so long as it can be provided to sufficiently press the tongue inside the mouth through the manipulation of the pressing unit 60.

The pressing head 64 may be fitted into the handle part 62. The handle part 62 may include mounting rods 62a extending in one direction, and the pressing head 64 may include mounting grooves 64b into which the mounting rods 62a are inserted. By inserting the mounting rods 62a into the mounting grooves 64b, the pressing head 64 may be coupled and fixed to the handle part 62. The pressing head 64 is detachably coupled to the handle part 62, such that the shape of the pressing head 64 may be mounted by changing and replacing according to the user's oral state. However, it is not limited thereto, and the pressing head 64 may be integrally formed with the handle part 62.

The pressing unit 60 may include a length adjustment part 66. Since a depth and an internal size of the mouth are different for each person, it is necessary to adjust an insertion length of the pressing unit 60. By adjusting the insertion length of the pressing unit 60 into the mouth through the length adjustment part 66, the position of the pressing head 64 may be changed.

The length adjustment part 66 may be provided in a groove shape on the outer circumferential surface of the handle part 62. The length adjustment part 66 may be formed as a plurality of grooves, and may be disposed to be spaced apart from each other in the longitudinal direction of the handle part 62. That is, the length adjustment part 66 may include a plurality of adjustment grooves 66a spaced apart from each other in an annular band shape. An insert protrusion 44a (see FIG. 3) formed in the mounting hole 44 of the mounting holder 40 may be inserted into the plurality of adjustment grooves 66a. Herein, the insert protrusion 44a is inserted into any one adjustment groove 66a of the plurality of adjustment grooves 66a, such that the length of the pressing unit 60 to be inserted into the mouth may be adjusted. The plurality of adjustment grooves 66a may be formed along the entire circumference of the outer circumferential surface of the handle part 62 for stable insertion of the insert protrusion 44a. The insert protrusion 44a may also be formed along the entire inner circumferential surface of the mounting hole 44 corresponding thereto.

Hereinafter, the rotational operation in the roll direction of the pressing unit of the oral fixation apparatus according to the present invention will be described.

Figure 8:
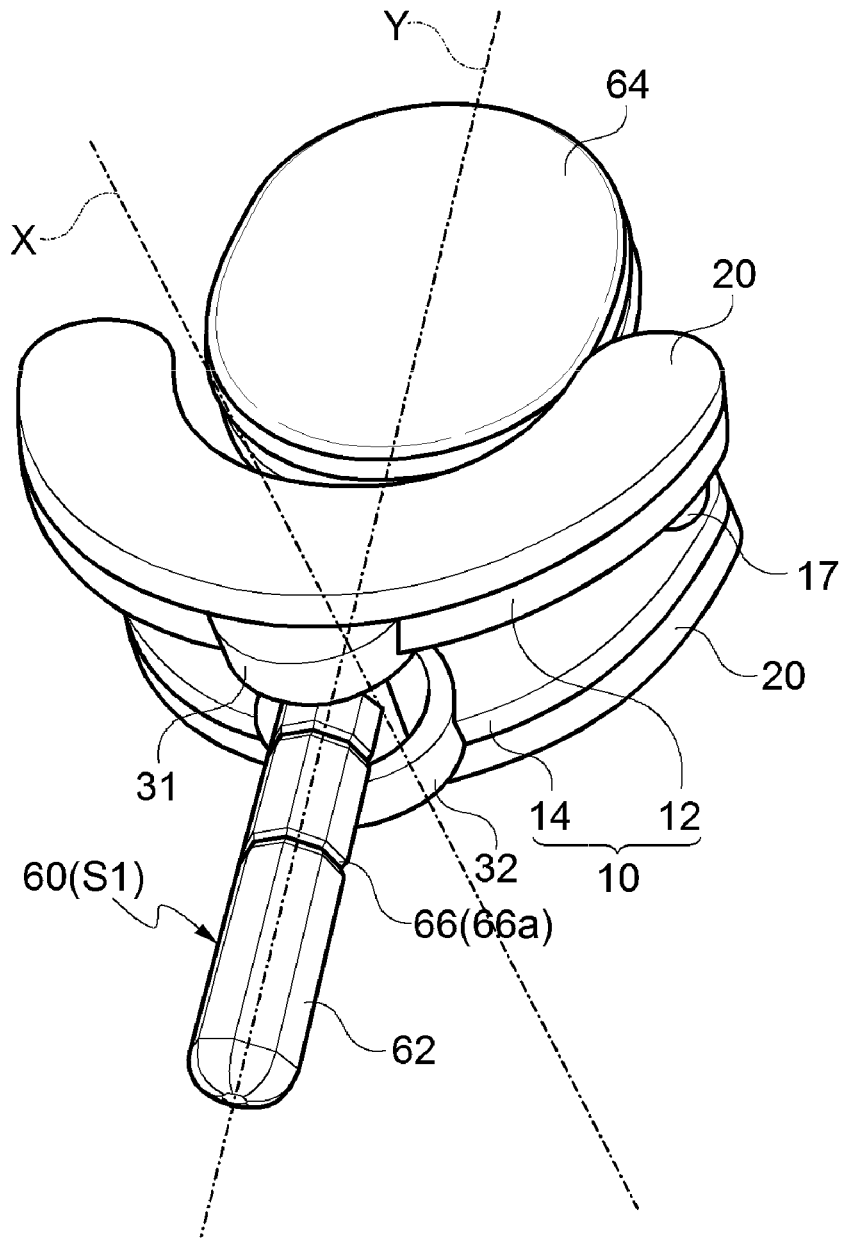
FIGS. 8 and 9 are perspective views illustrating states in which the pressing unit of the oral fixation apparatus according to an embodiment of the present invention is rotated in a roll direction.
Figure 9:
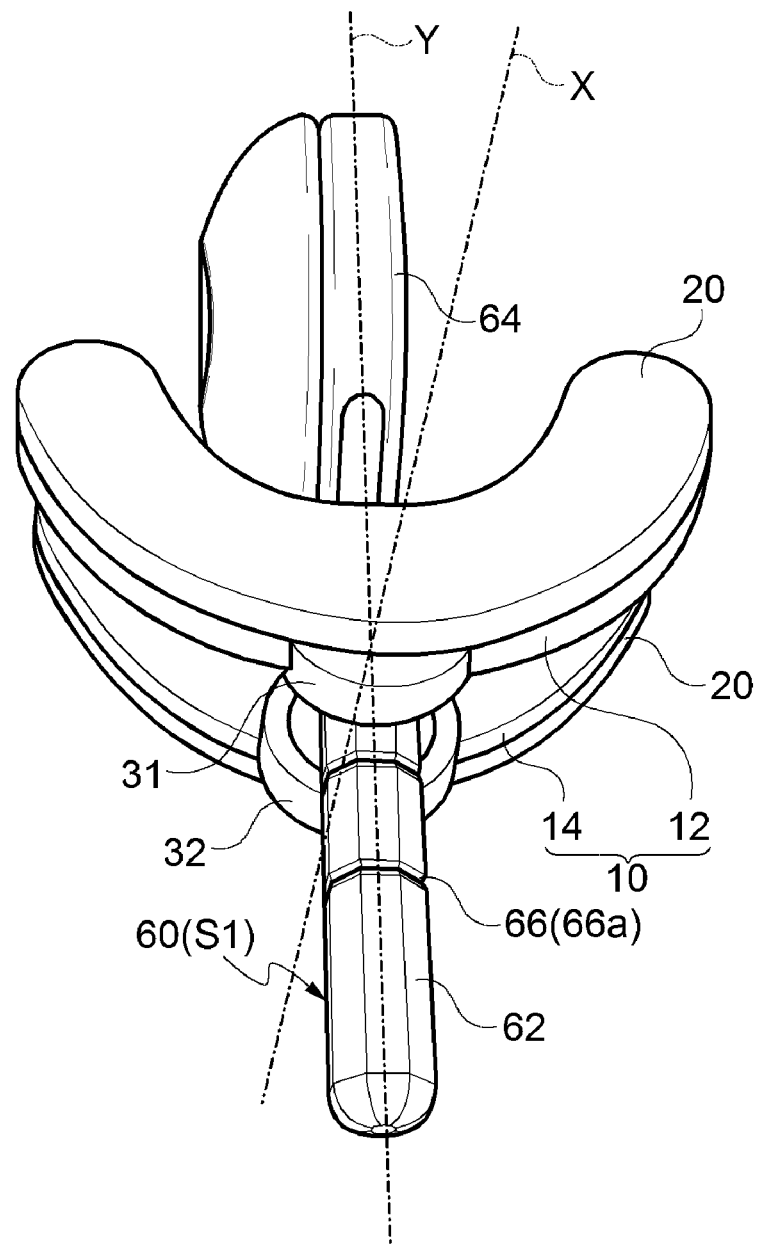

FIGS. 8 and 9 are perspective views illustrating states in which the pressing unit of the oral fixation apparatus according to an embodiment of the present invention is rotated in the roll direction.

As described above, the handle part 62 and the mounting hole 44 may be formed in a polygonal shape corresponding to each other. The pressing unit 60 of a first state S1 is separated from the mounting holder 40 as shown in FIG. 8, then the pressing unit 60 of a second state S2 rotated in the roll direction is mounted in the mounting holder 40 as shown in FIG. 9. Through this operation, it is possible to adjust a direction in which the pressing head 64 of the pressing unit 60 faces in the mouth. Since the handle part 62 and the mounting hole 44 are formed in the polygonal shapes corresponding to each other, rotation of the pressing unit 60 in the roll direction may be limited while it is mounted in the mounting hole 44.

Hereinafter, the rotational operation in the yaw direction of the pressing unit 60 of the oral fixation apparatus 1 according to the present invention will be described.

Figure 10:
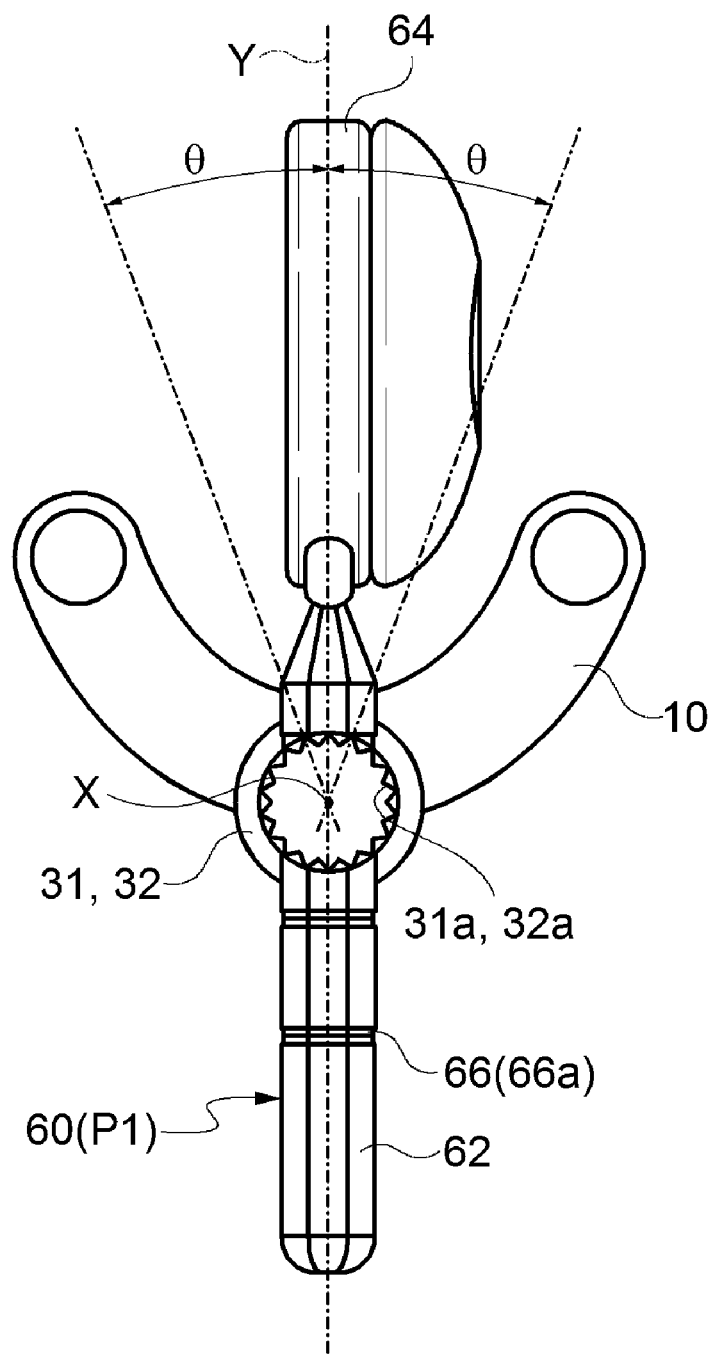
FIGS. 10, 11 and 12 are plan views illustrating states in which the pressing unit of the oral fixation apparatus according to an embodiment of the present invention is rotated in a yaw direction.
Figure 11:
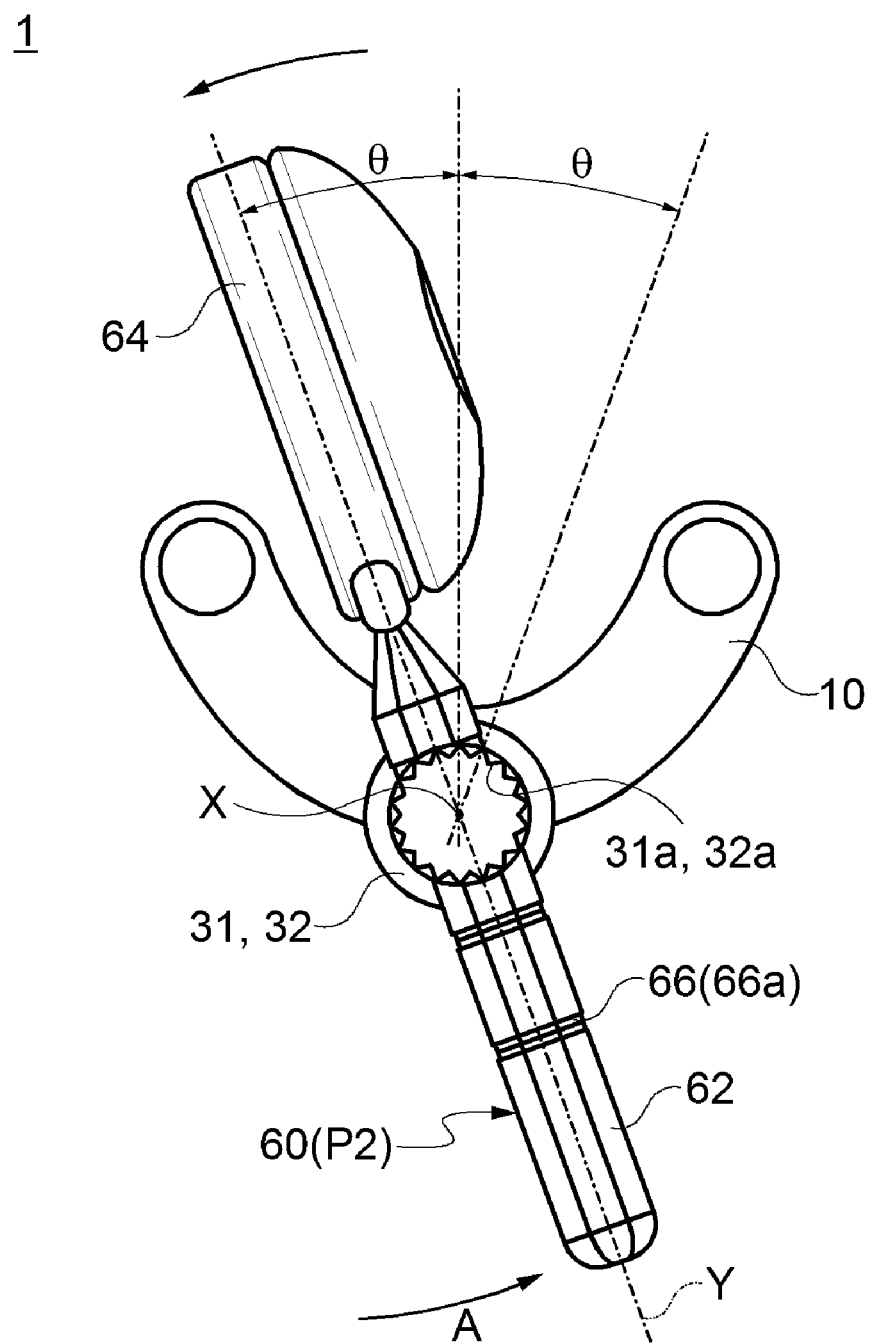
Figure 12:
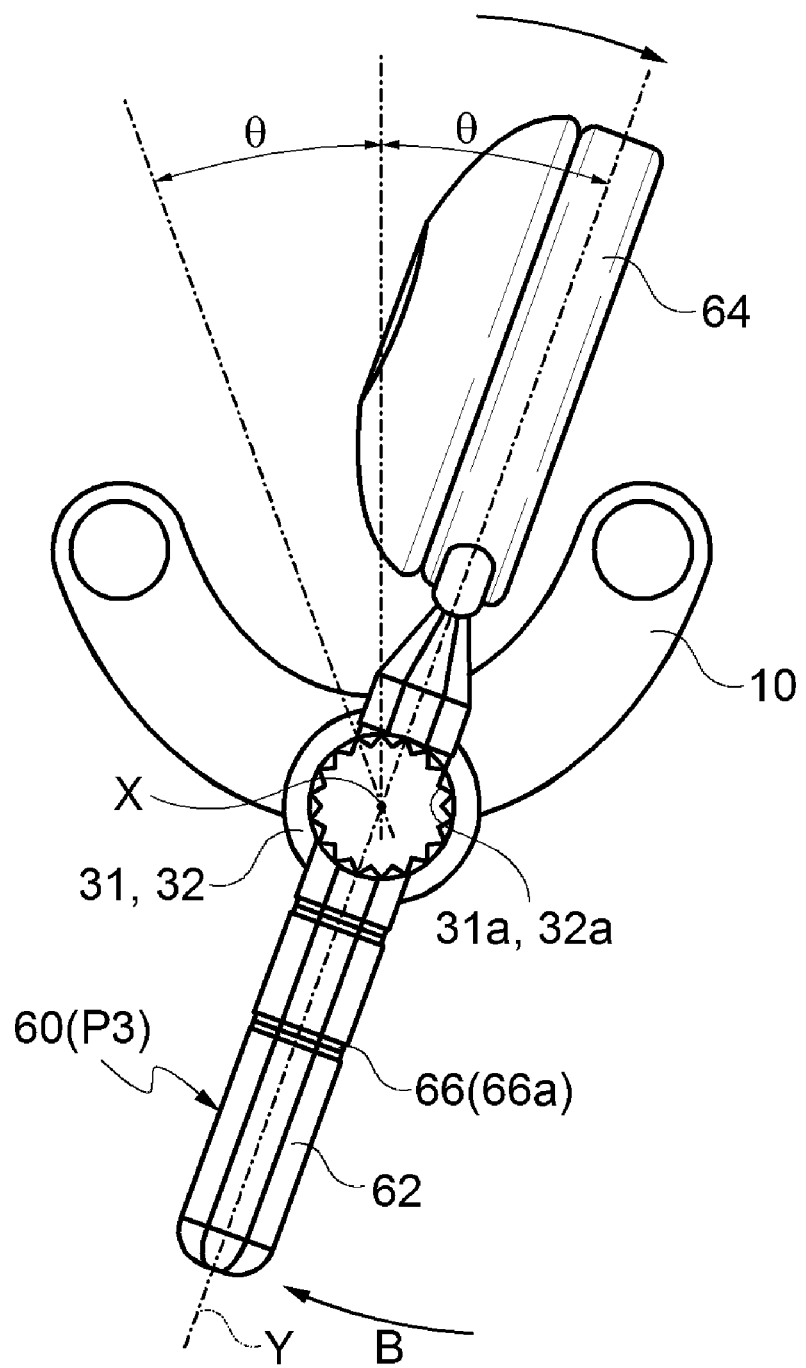

FIGS. 10, 11 and 12 are plan views illustrating states in which the pressing unit of the oral fixation apparatus according to an embodiment of the present invention is rotated in the yaw direction.

The first and second mounting parts 46a and 46b of the mounting holder 40 are provided rotatable relative to the first and second guide parts 31 and 32, respectively. Specifically, when the longitudinal direction of the mounting holder 40 is referred to as the X-axis direction, the pressing unit 60 mounted in the mounting holder 40 is provided to rotate about the X-axis on the plane perpendicular to the X-axis.

When an external force is applied to the handle part 62 in an A direction relative to the pressing unit 60 at a first position P1 shown in FIG. 10, the pressing unit 60 becomes a second position P2 by rotating from the first position P1 about the X axis as shown in FIG. 11.

Further, when an external force is applied to the handle part 62 in a B direction relative to the pressing unit 60 at the first position P1, the pressing unit 60 becomes a third position P3 by rotating from the first position P1 about the X axis as shown in FIG. 12.

The pressing unit 60 rotated to the first to third positions P1, P2 and P3 may be held in the rotated position by the engaging gears 48a and 48b formed in the mounting holder 40 and the gear grooves 31a and 32a formed in the rotation guide 30. Since the plurality of engaging gears 48a and 48b and the plurality of gear grooves 31a and 32a are provided, the pressing unit 60 may be rotated finely and fixed in the yaw direction. In the present embodiment, the configuration, in which the pressing unit 60 is rotated to the second position or the third position by the same 0 from the first position in the yaw direction, has been described as an example. However, it is not limited thereto, and a rotation amount thereof leftward and rightward in the yaw direction may be set differently, and a rotation magnitude thereof is not limited.

After removing the oral fixation apparatus 1 from the mouth, when mounting it again in the mouth, by rotating the pressing unit 60 by the existing rotation amount, it is possible to maintain the same state inside the mouth.

Hereinafter, the length adjustment of the pressing unit in the oral fixation apparatus of the present invention will be described.

Figure 13:
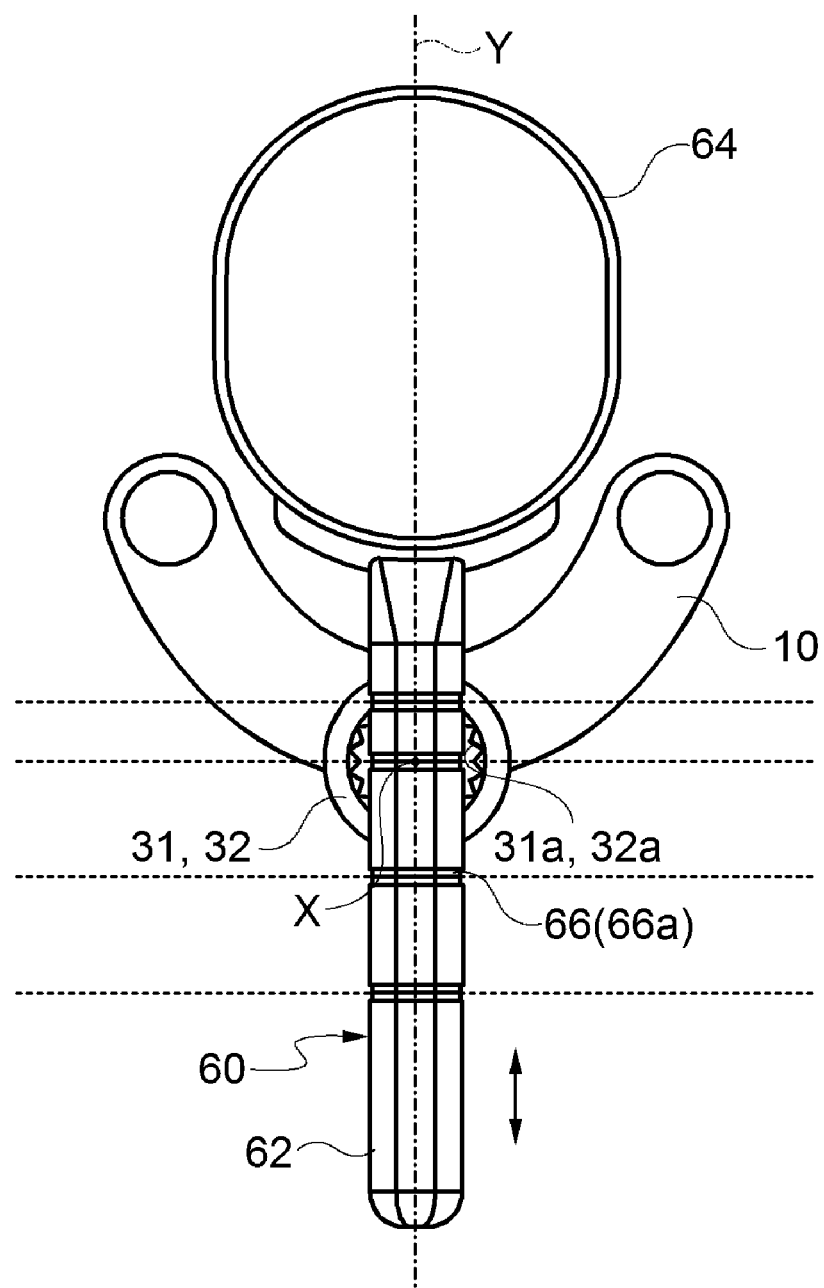
FIG. 13 is a plan view illustrating the principle of adjusting a length of the pressing unit of the oral fixation apparatus according to an embodiment of the present invention.

FIG. 13 is a plan view illustrating the principle of adjusting a length of the pressing unit of the oral fixation apparatus according to an embodiment of the present invention.

As described above, the length adjustment part 66 may be formed in the pressing unit 60. The insert protrusion 44a corresponding to the plurality of adjustment grooves 66a may be formed in the mounting hole 44 of the mounting holder 40. The insert protrusion 44a is inserted into any one adjustment groove 66a of the plurality of adjustment grooves 66a, such that it is possible to prevent the pressing unit 60 from moving in the longitudinal direction of the pressing unit 60 relative to the mounting holder 40.

For adjusting the length, when an external force is applied to the pressing unit 60 to push or pull it in a Y-axis direction which is the longitudinal direction, the insert protrusion 44a is separated from any one length adjustment groove 66a, and is inserted into another length adjustment groove 66a disposed on a movement path of the pressing unit 60. By repeating this operation, it is possible to adjust the insertion length of the pressing unit 60 according to the oral state of the subject.

The oral fixation apparatus 1 may be disposed in the mouth by the reference groove 22 of the shape holding part 20 at the same level despite the repeated detachment. In addition, since the oral fixation apparatus 1 is located at the same position, it is possible to prevent the reference point of the X and Y axes formed by the mouthpiece 10 and the pressing unit 60 of the oral fixation apparatus 1 from being deformed. Further, since the same reference point of the X and Y axes is maintained, it is possible to maintain the same intraoral state only by applying the preset rotation amount or length adjustment amount of the pressing unit 60.

Hereinafter, an oral fixation apparatus according to another embodiment of the present invention will be described. In the description below, the same components or same configurations as those of the previous embodiment will not be redundantly described. The present embodiment is different from the embodiment described above in terms of specific configuration, but is operated in the same manner. Therefore, specific operations in the present embodiment will not be described.

Figure 14:
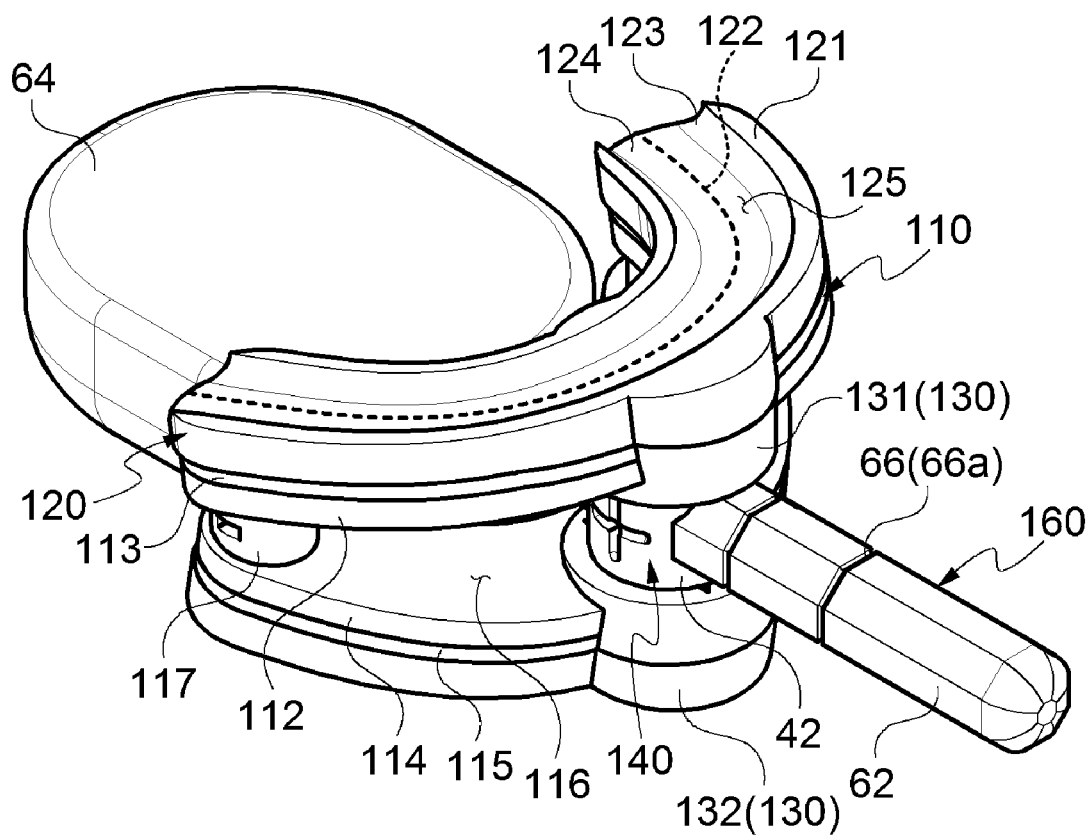
FIG. 14 is a perspective view of an oral fixation apparatus according to another embodiment of the present invention.
Figure 15:
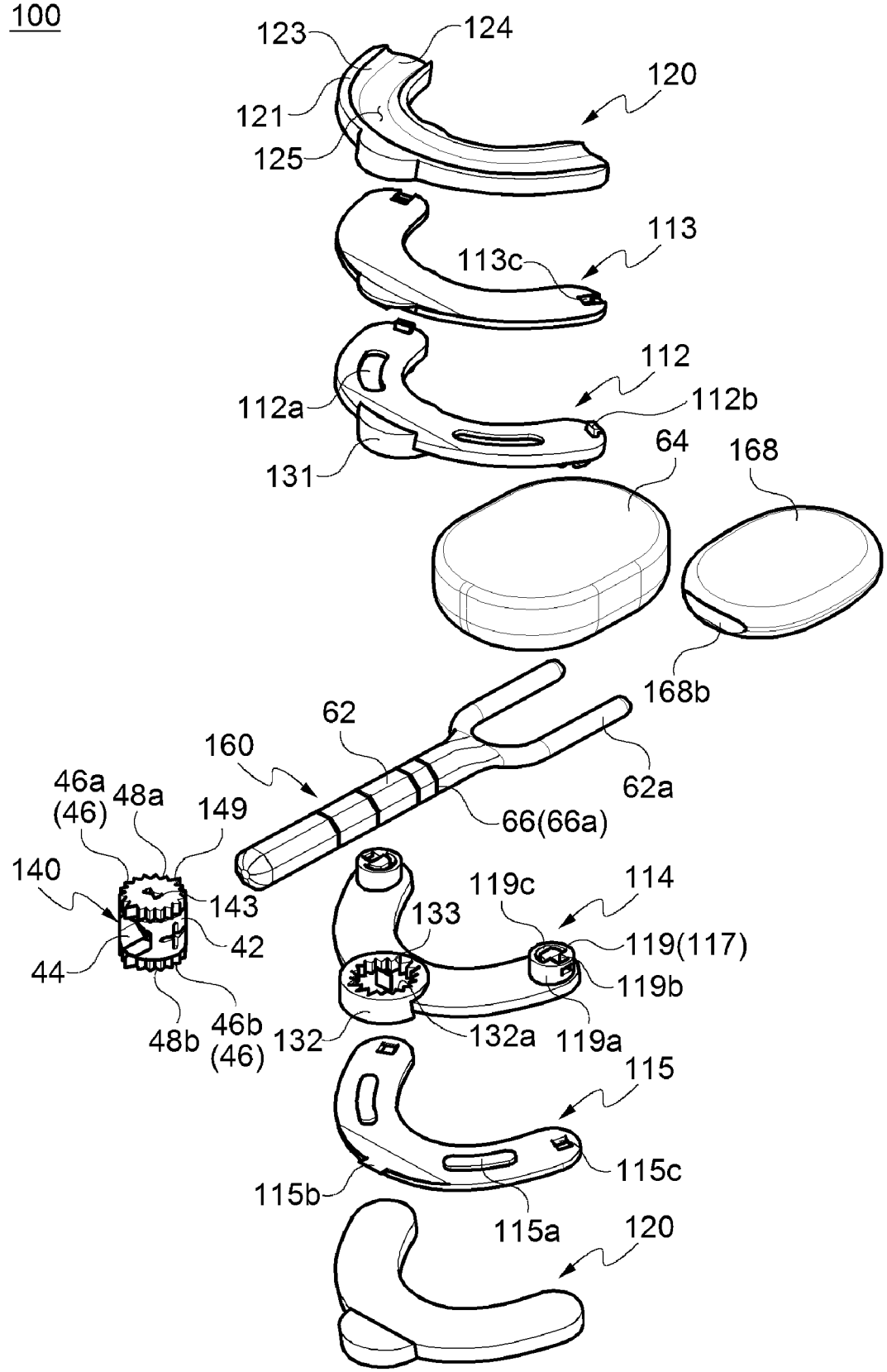
FIG. 15 is an exploded perspective view of the oral fixation apparatus according to another embodiment of the present invention.

FIG. 14 is a perspective view of an oral fixation apparatus according to another embodiment of the present invention, and FIG. 15 is an exploded perspective view of the oral fixation apparatus according to another embodiment of the present invention.

An oral fixation apparatus 100 is configured to be inserted into the mouth. The oral fixation apparatus 100 may maintain the same intraoral state upon repeated radiation therapy.

The oral fixation apparatus 100 may include a mouthpiece 110 and a pressing unit 160.

The mouthpiece 110 may include a first body 112 corresponding to the upper teeth and a second body 114 corresponding to the lower teeth.

The mouthpiece 110 may include first and second guide bodies 113 and 115. The first and second guide bodies 113 and 115 may be located between the first and second bodies 112 and 114 and shape holding parts 120 corresponding to the first and second bodies 112 and 114, respectively. The first and second guide bodies 113 and 115 may be detachably coupled to the first and second bodies 112 and 114, respectively. The shape holding parts 120 may be detachably coupled to the first and second bodies 112 and 114 together with the first and second guide bodies 113 and 115. Through this configuration, the shape holding parts 120 and the first and second bodies 112 and 114 may be easily separated.

Figure 16:
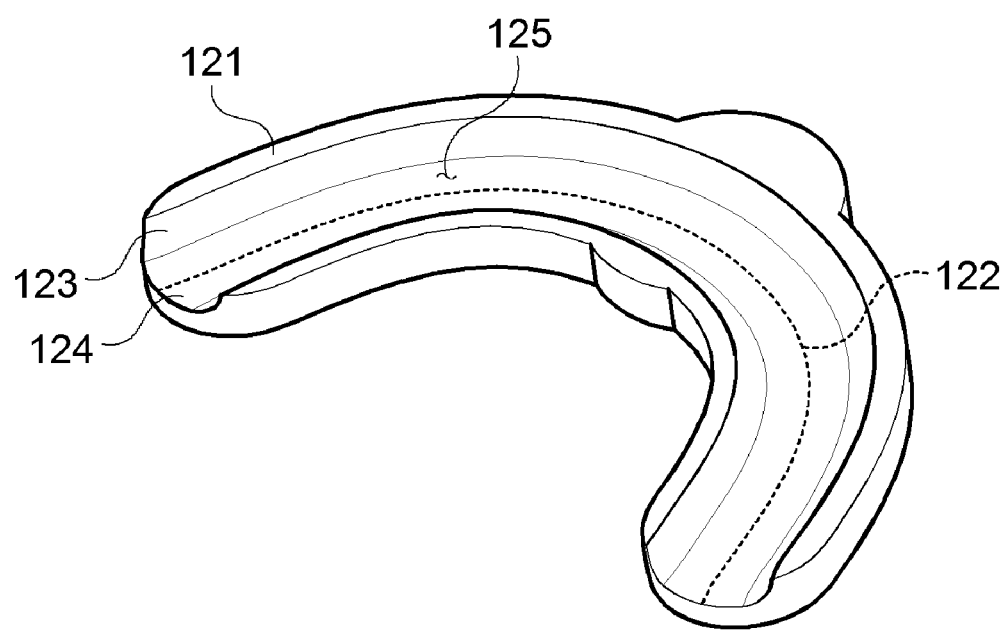
FIG. 16 is a perspective view illustrating a shape holding part of the oral fixation apparatus according to another embodiment of the present invention.

FIG. 16 is a perspective view illustrating a shape holding part of the oral fixation apparatus according to another embodiment of the present invention.

The mouthpiece 110 may include the shape holding part 120 for taking an impression.

Unlike the shape holding part 20 in the previous embodiment, the shape holding part 120 may have a concavely formed surface in contact with the teeth. That is, the shape holding part 120 may include inclined surfaces 123 slantly formed on a surface thereof to guide the teeth inserted into the body thereof, and a seat surface 124 connected to the inclined surfaces 123, on which the teeth are seated. Herein, a pair of inclined surfaces 123 may be provided, and the seat surface 124 may be disposed between the pair of inclined surfaces 123. The inclined surface 123 and the seat surface 124 may be formed longitudinally in the direction of the row of teeth. The inclined surface 123 and the seat surface 124 may define an insertion space 125 concave relative to the body of the shape holding part 120. The teeth may be inserted into the insertion space 125. The inclined surface 123 may guide the teeth inserted into the insertion space 125 to the seat surface 124.

When the teeth is inserted into the insertion space 125, the shape holding part 120 may include a reference groove 122 corresponding to the teeth of the subject. The reference groove 122 may be formed in a shape corresponding to the row of teeth of the subject. The reference groove 122 may be formed on the seat surface 124, and may be formed in a shape of a more concave groove than the seat surface 124 by being pressed by the teeth. The shape holding part 120 may be cured in a state in which the reference groove 122 is formed. The cured shape holding part 120 may allow the oral fixation apparatus 100 to be located at the same position and arrangement in the user's mouth upon repeated radiation therapy.

The shape holding part 120 may be configured to cover an upper surface of the first guide body 113 and a lower surface of the second guide body 115. Specifically, the shape holding part 120 may be configured to cover the entire upper surface of the first guide body 113 and the entire lower surface of the second guide body 115. Through this configuration, forces transmitted from the upper and lower teeth to the shape holding part 120 are uniformly transmitted to the first and second guide bodies 113 and 115 and the first and second bodies 112 and 114, such that the oral fixation apparatus 100 may stably support the inside of the mouth.

Figure 17:
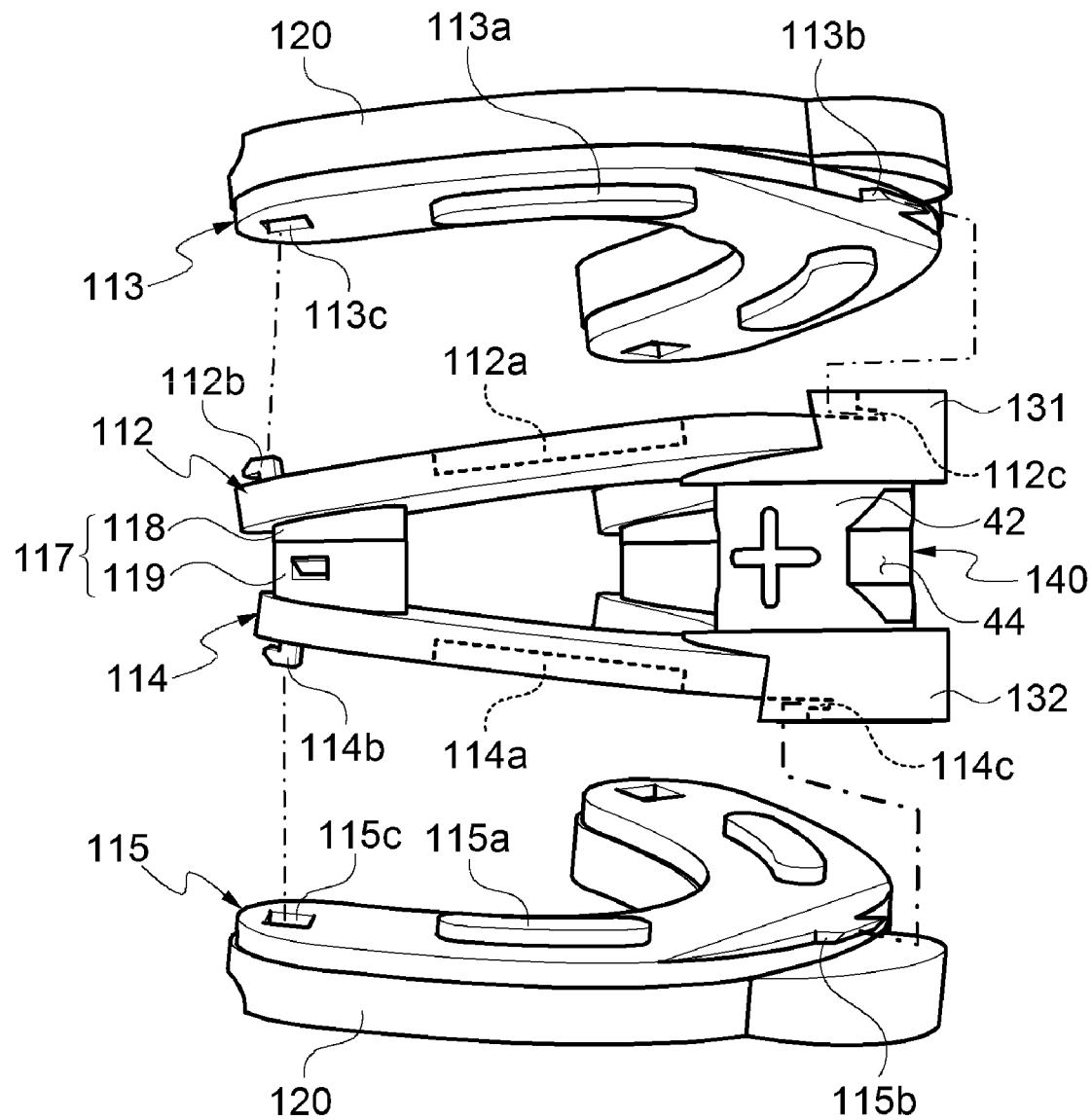
FIG. 17 is a partially exploded perspective view of a mouthpiece of an oral fixation apparatus according to another embodiment of the present invention.
Figure 18:
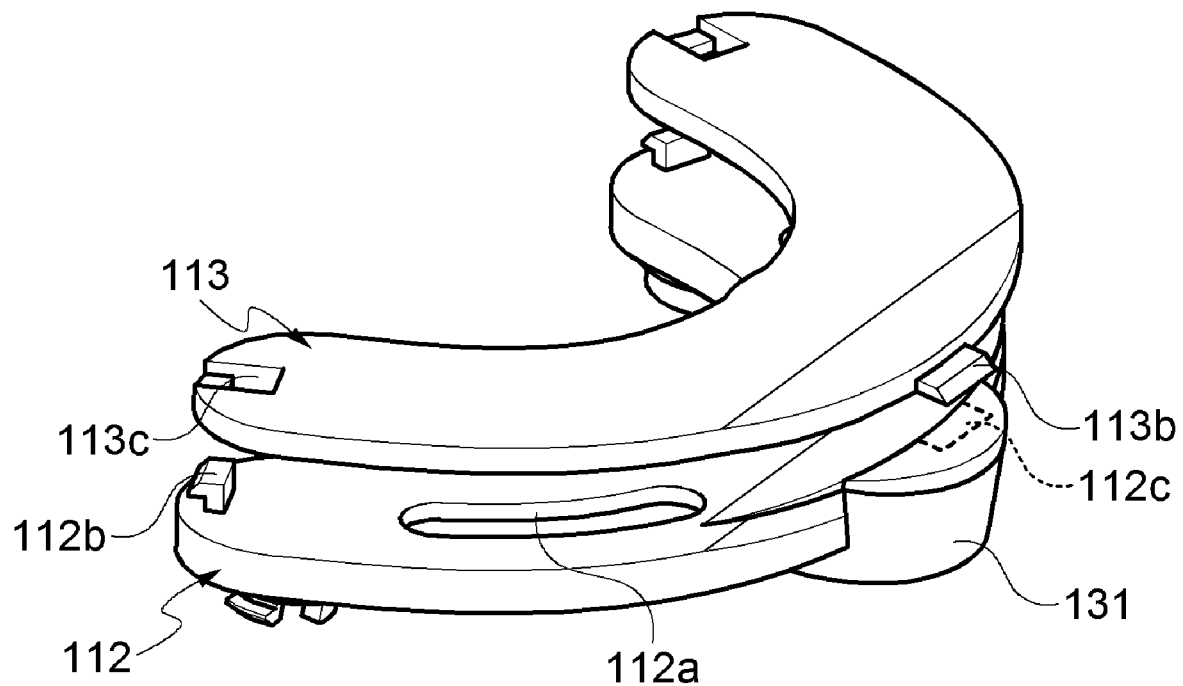
FIGS. 18 and 19 are perspective views illustrating a coupling process of the mouthpiece of the oral fixation apparatus according to another embodiment of the present invention.
Figure 19:
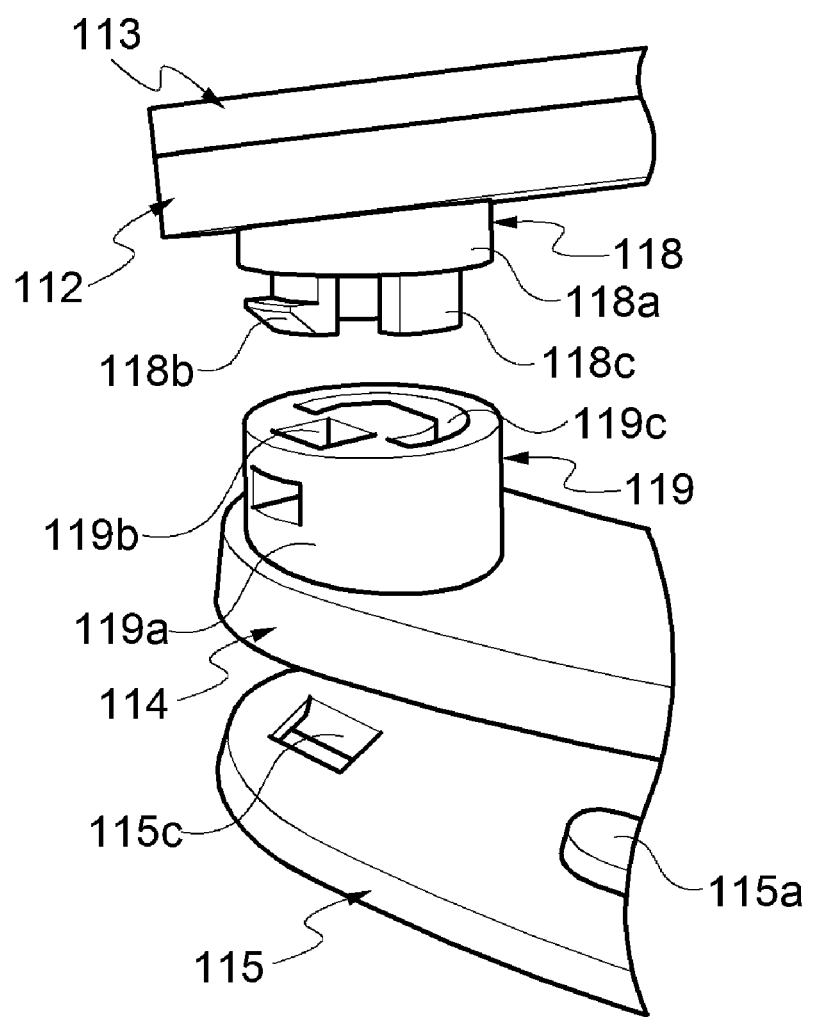

FIG. 17 is a partially exploded perspective view of a mouthpiece of an oral fixation apparatus according to another embodiment of the present invention, and FIGS. 18 and 19 are perspective views illustrating a coupling process of the mouthpiece of the oral fixation apparatus according to another embodiment of the present invention.

First and second guide bodies 113 and 115 may be detachably coupled to first and second bodies 112 and 114, respectively. The first and second guide bodies 113 and 115 and the first and second bodies 112 and 114 may include coupling means for detachably coupling these bodies with each other.

The coupling means may include guide protrusions 113*a* and 115*a* and guide grooves 112*a* and 114*a*. The first and second guide bodies 113 and 115 may include the guide protrusions 113*a* and 115*a* formed to protrude from surfaces thereof facing the first and second bodies 112 and 114. The guide protrusions 113*a* and 115*a* may be formed on the first and second guide bodies 113 and 115 in the longitudinal direction of the first and second guide bodies 113 and 115. The first and second bodies 112 and 114 may include the guide grooves 112*a* and 114*a* concavely formed in surfaces thereof facing the first and second guide bodies 113 and 115 so that the guide protrusions 113*a* and 115*a* are inserted therein. The guide grooves 112*a* and 114*a* may be formed in the longitudinal direction of the first and second bodies 112 and 114 corresponding to the guide protrusions 113*a* and 115*a*.

The guide protrusions 113*a* and 115*a* are inserted into the guide grooves 112*a* and 114*a*, such that the first and second guide bodies 113 and 115 may be stably seated on the first and second bodies 112 and 114. A pair of guide protrusions 113*a* and 115*a* and a pair of guide grooves 112*a* and 114*a* may be provided in the first and second guide bodies 113 and 115 and the first and second bodies 112 and 114, respectively.

The coupling means may include coupling hooks and coupling grooves.

The first and second guide bodies 113 and 115 may include first coupling hooks 113*b* and 115*b*, and a pair of first coupling grooves 113*c* and 115*c*, respectively. The first and second bodies 112 and 114 may include second coupling grooves 112*c* and 114*c* into which the first coupling hooks 113*b* and 115*b* are inserted and fixed, and a pair of second coupling hooks 112*b* and 114*b* inserted into the pair of first coupling grooves 113*c* and 115*c*, respectively The first coupling hooks 113*b* and 115*b* may be located on the side portions of the front teeth in the first and second guide bodies 113 and 115, and the second coupling grooves 112*c* and 114*c* may also be located on the side portions of the front teeth in the first and second bodies 112 and 114. The pair of first coupling grooves 113*c* and 115*c* may be located on the side portions of the back teeth in the first and second guide bodies 113 and 115, and the pair of second coupling hooks 112*b* and 114*b* may be located on the side portions of the back teeth in the first and second bodies 112 and 114.

In the present embodiment, the coupling hooks and the coupling grooves are arranged to be distributed in a triangular shape. As described above, the coupling hooks and the coupling grooves are disposed to be spaced apart from each other in the first and second bodies 112 and 114 and the first and second guide bodies 113 and 115, respectively, such that the first and second guide bodies 113 and 115 may be stably coupled to the first and second bodies 112 and 114 in a detachable manner.

In the drawings and description of the present embodiment, for the convenience of illustration and description, the number and arrangement of the guide protrusions 113*a* and 115*a*, guide grooves 112*a* and 114*a*, coupling hooks, and coupling grooves have been described. However, the number and arrangement thereof are not limited thereto. Any configuration may be used so long as it can sufficiently and stably couple the first and second guide bodies 113 and 115 to the first and second bodies 112 and 114 in the detachable manner. For example, the guide protrusions 113*a* and 115*a* may be disposed on the first and second bodies 112 and 114; and the guide grooves 112*a* and 114*a* may be disposed in the first and second guide bodies 113 and 115. In addition, the first coupling hooks 113*b* and 115*b*, and the first coupling grooves 113*c* and 115*c* may be disposed in the first and second bodies 112 and 114; and the second coupling grooves 112*c* and 114*c*, and the second coupling hooks 112*b* and 114*b* may be disposed in the first and second guide bodies 113 and 115, respectively.

The mouthpiece 110 may include a connection part 117 which is provided on a rear side of the first and second bodies 112 and 114 to support the first and second bodies 112 and 114.

The connection part 117 may include a first connection part 118 extending downward from the first body 112 and a second connection part 119 extending upward from the second body 114.

The first connection part 118 may include an engaging hook 118*b* and a rib 118*c*. The engaging hook 118*b* and the rib 118*c* may be configured to protrude from the body of the first connection part 118 toward the second body 114, respectively. The rib 118*c* may be formed in a curved surface, and may be configured so that a concave portion thereof faces the engaging hook 118*b*. The rib 118*c* may be formed to have a shape of an arc whose cross section has a predetermined radius around the engaging hook 118*b*. Through this configuration, a load applied to the connection part 117 is dispersed, such that the first and second connection parts 118 and 119 may be securely coupled. Since a pair of first connection parts 118 are provided in the first body 112, a pair of engaging hooks 118*b* and ribs 118*c* may also be provided, respectively.

The pair of engaging hooks 118*b* may be disposed to face directions opposite to each other. In the present embodiment, the pair of engaging hooks 118*b* may be configured so that a hook shape thereof faces outward of the first and second bodies 112 and 114.

In addition, a pair of ribs 118*c* may also be disposed to face directions opposite to each other. In the present embodiment, the pair of ribs 118*c* may be configured so that a convex surface thereof faces inward of the first and second bodies 112 and 114.

The second connection part 119 may include an engaging groove 119*b* and an insertion groove 119*c*. The engaging hook 118*b* may be inserted into and engaged to the engaging groove 119*b*. A pair of engaging grooves 119*b* may be provided to correspond to the pair of engaging hooks 118*b*. The pair of engaging grooves 119*b* may be formed in directions opposite to each other corresponding to the pair of engaging hooks 118*b*. In the present embodiment, the pair of engaging grooves 119*b* may be configured so that the pair of engaging hooks 118*b* facing outward are respectively engaged thereto.

The insertion groove 119*c* is configured to allow the rib 118*c* to be inserted therein. The insertion groove 119*c* may be formed to have an arc shape whose cross-section has a predetermined radius corresponding to the shape of the rib 118*c*. A pair of insertion grooves 119*c* may be provided to correspond to the pair of ribs 118*c*. The pair of insertion grooves 119c may be formed in directions opposite to each other corresponding to the pair of ribs 118c. In the present embodiment, the pair of ribs 118c facing inward may be configured to allow the pair of insertion grooves 119c to be respectively inserted therein.

The first and second connection parts 118 and 119 may be detachably coupled to each other through the configurations of the engaging hook 118b, the engaging groove 119b, the rib 118c, and the insertion groove 119c. In addition, the engaging hook 118b is coupled to the engaging groove 119b, and the rib 118c is coupled to the insertion groove 119c, such that double coupling is possible, and thereby the first and second bodies 112 and 114 may be securely coupled to each other.

The pair of engaging hooks 118b, engaging grooves 119b, ribs 118c, and insertion grooves 119c are respectively disposed opposite to each other in the mouthpiece 11, such that these configurations may be securely coupled to the corresponding configurations.

Figure 20:
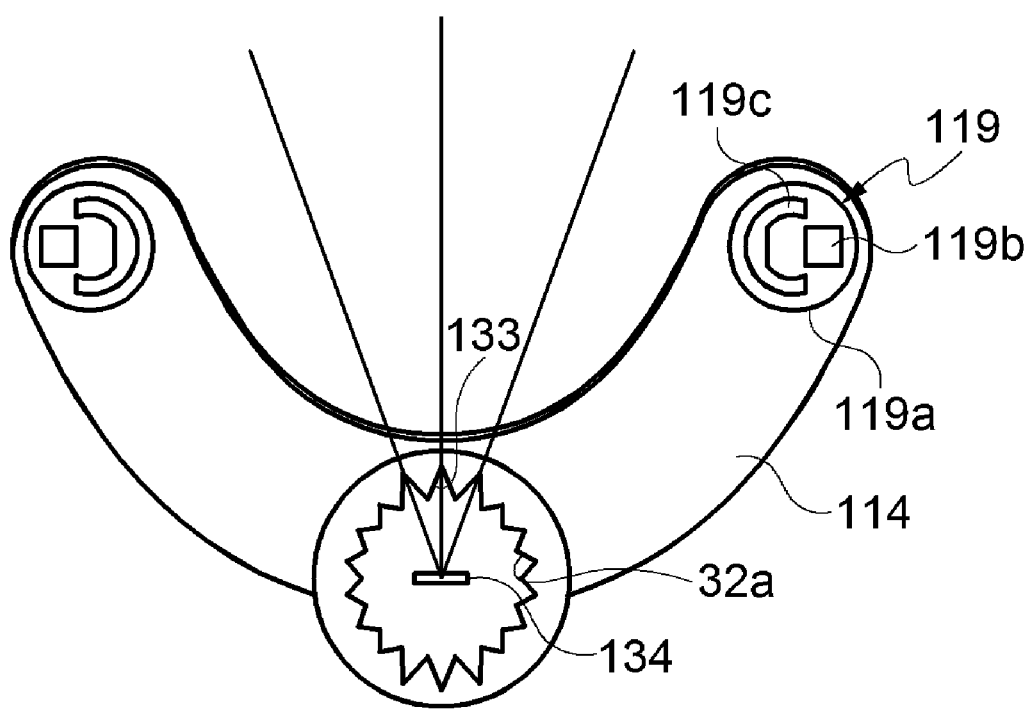
FIGS. 20 and 21 are plan views illustrating the principle of rotation of a mounting holder of an oral fixation apparatus according to another embodiment of the present invention in the yaw direction.
Figure 21:
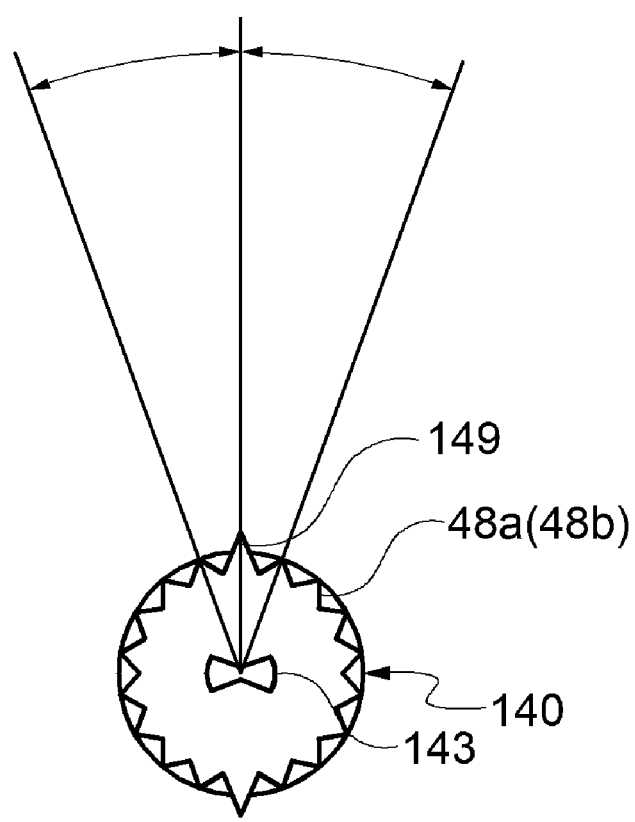

FIGS. 20 and 21 are plan views illustrating the principle of rotation of a mounting holder of an oral fixation apparatus according to another embodiment of the present invention in the yaw direction.

The oral fixation apparatus 100 may include a rotation guide 130. The rotation guide 130 may include first and second guide parts 131 and 132. The first and second guide parts 131 and 132 may include gear grooves 31a and 32a arranged alternately in inner circumferential surfaces thereof in the circumferential direction.

The rotation guide 130 may include a rotation protrusion 134 formed to protrude from a surface on which the mounting part 46 of the mounting holder 140 is mounted. The rotation protrusion 134 may be configured to be fixed to a surface facing the mounting part 46 in the rotation guide 130. The rotation protrusion 134 may be configured to be inserted into a rotation stopper 143 of the mounting holder 140, which will be described below. The rotation protrusion 134 may be formed in a plate shape.

The mounting holder 140 may be located in front of the first and second bodies 112 and 114, that is, corresponding to the side portions of the front teeth. The mounting holder 140 is formed in a substantially column shape, and is configured so as to connect the first and second bodies 112 and 114 while maintaining the state in which they are spaced apart from each other at a predetermined angle together with the connection parts 117.

The mounting holder 140 may include a holder body 42 (see FIG. 15) that forms a body thereof, a mounting hole 44 (see FIG. 15), and a mounting part 46 (see FIG. 15).

The mounting holder 140 may include the rotation stopper 143 formed in at least one surface of both surfaces, i.e., one surface and the other surface of the holder body 42. The above-described rotation protrusion 134 may be inserted into the rotation stopper 143. When rotating the mounting holder 140 in the yaw direction, rotation of the rotation protrusion 134 is limited by the rotation stopper 143, and the rotation stopper 143 is configured to prevent the rotation protrusion 134 from rotating more than a predetermined range. The rotation stopper 143 may be formed in a symmetrical sector shape, and thus may be configured so as to limit the rotation of the rotation protrusion 134 by a surface forming a radius thereof.

The engaging gears 48a and 48b of the mounting holder 140 may include adjustment gears 149. The adjustment gear 149 may be formed with a longer length than that of the adjacent engaging gears 48a and 48b so as to protrude outward therefrom. The adjustment gear 149 may refer to one tooth having a long protrusion length among the engaging gears 48a and 48b. At least one adjustment gear 149 may be provided, which can be inserted into any one adjustment groove 133 among a plurality of adjustment grooves 133 to be described below.

The gear grooves 31a and 32a of the rotation guide 130 may include adjustment grooves 133. The adjustment groove 133 may be formed with a deeper depth than that of the adjacent gear grooves 31a and 32a. The adjustment groove 133 may refer to a plurality of teeth having a deep depth among the gear grooves 31a and 32a. A plurality of adjustment grooves 133 may be continuously arranged. The adjustment gear 149 is inserted into any one adjustment groove 133 among the plurality of adjustment grooves 133. Thereby, when the mounting holder 140 and the pressing unit 160 rotate in the yaw direction relative to the rotation guide 130, it is possible to accurately adjust the rotation angle, and reproduce the same rotation angle in the yaw direction of the oral fixation apparatus 100 upon the repeated radiation therapy.

Figure 22:
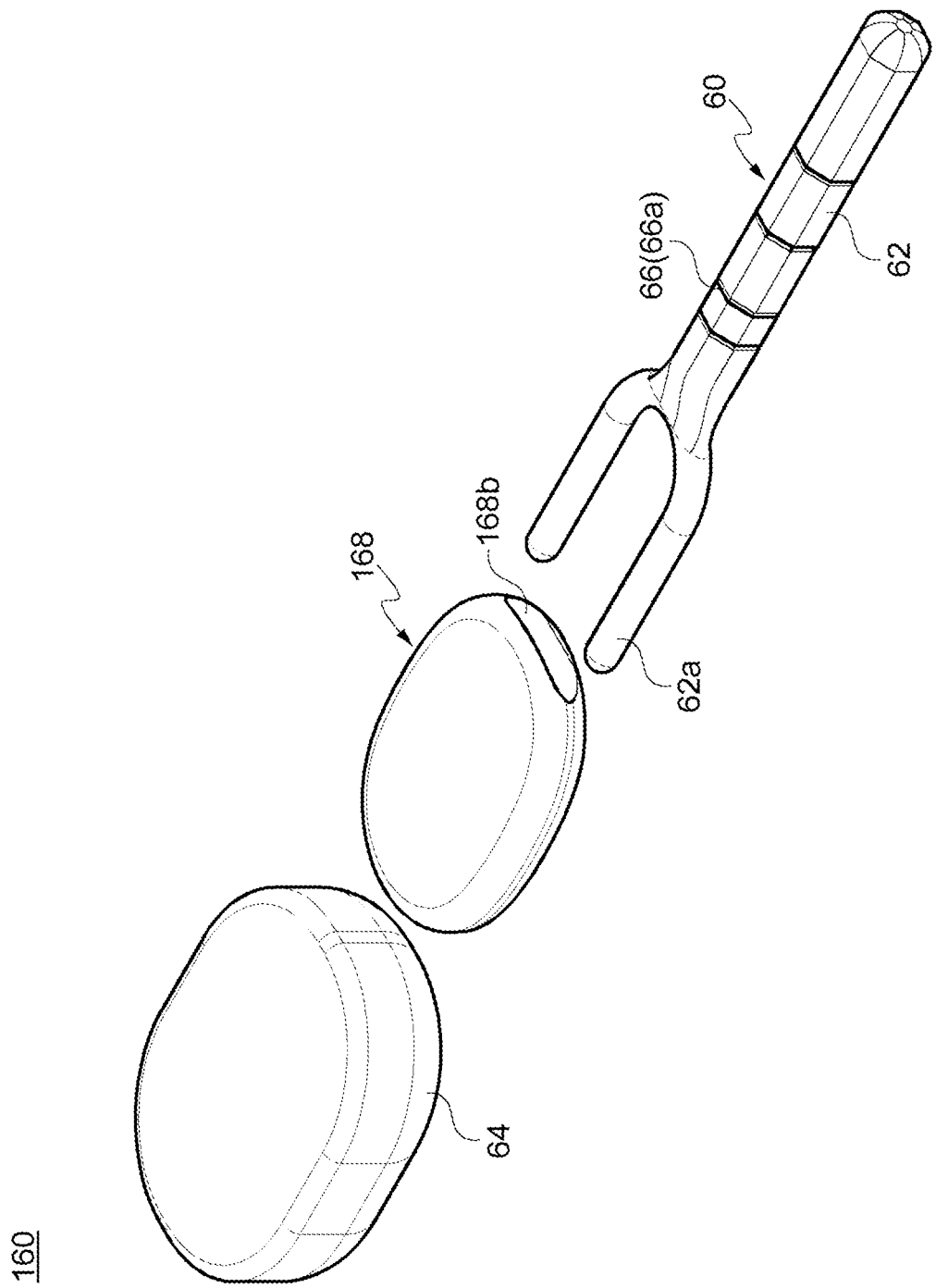
FIG. 22 is an exploded perspective view illustrating a pressing unit of the oral fixation apparatus according to another embodiment of the present invention.

FIG. 22 is an exploded perspective view illustrating a pressing unit 100 of the oral fixation apparatus 100 according to another embodiment of the present invention.

The pressing unit 160 may include a handle part 62 and a pressing head 64.

The handle part 62 is configured to allow the user to grip, and when an external force is applied, the pressing unit 160 is provided to be rotated in the yaw direction, as described above. When the oral fixation apparatus 100 is mounted in the mouth, the handle part 62 is provided to be exposed to an outside of the mouth. Through this configuration, it is possible to control the intraoral state by manipulating the handle part 62. Further, it is possible to manipulate the handle part 62 so as to be the state rotated in the roll direction relative to the mounting holder 140.

The pressing unit 160 may include a holder 168. The holder 168 may be fitted to the handle part 62. The handle part 62 may include a mounting rod 62a protruding in one direction, and the holder 168 may include a mounting groove 168b into which the mounting rod 62a is inserted. By inserting the mounting rod 62a into the mounting groove 168b, the holder 168 may be coupled and fixed to the handle part 62.

The pressing head 64 may be mounted on the holder 168 coupled to the handle part 62. The pressing head 64 may be made of a thermoplastic and cured after the holder 168 is inserted. The cured pressing head 64 may be integrally formed with the holder 168. The holder 168 is detachably coupled to the handle part 62, such that the holder 168 may be separated from the handle part 62 as necessary. Thereby, the holder 168 and the pressing head 64 may be replaced by new ones.

Hereinafter, an oral fixation apparatus according to another embodiment of the present invention will be described. In the description below, the same components or same configurations as those of the previous embodiment will not be redundantly described.

Figure 23:
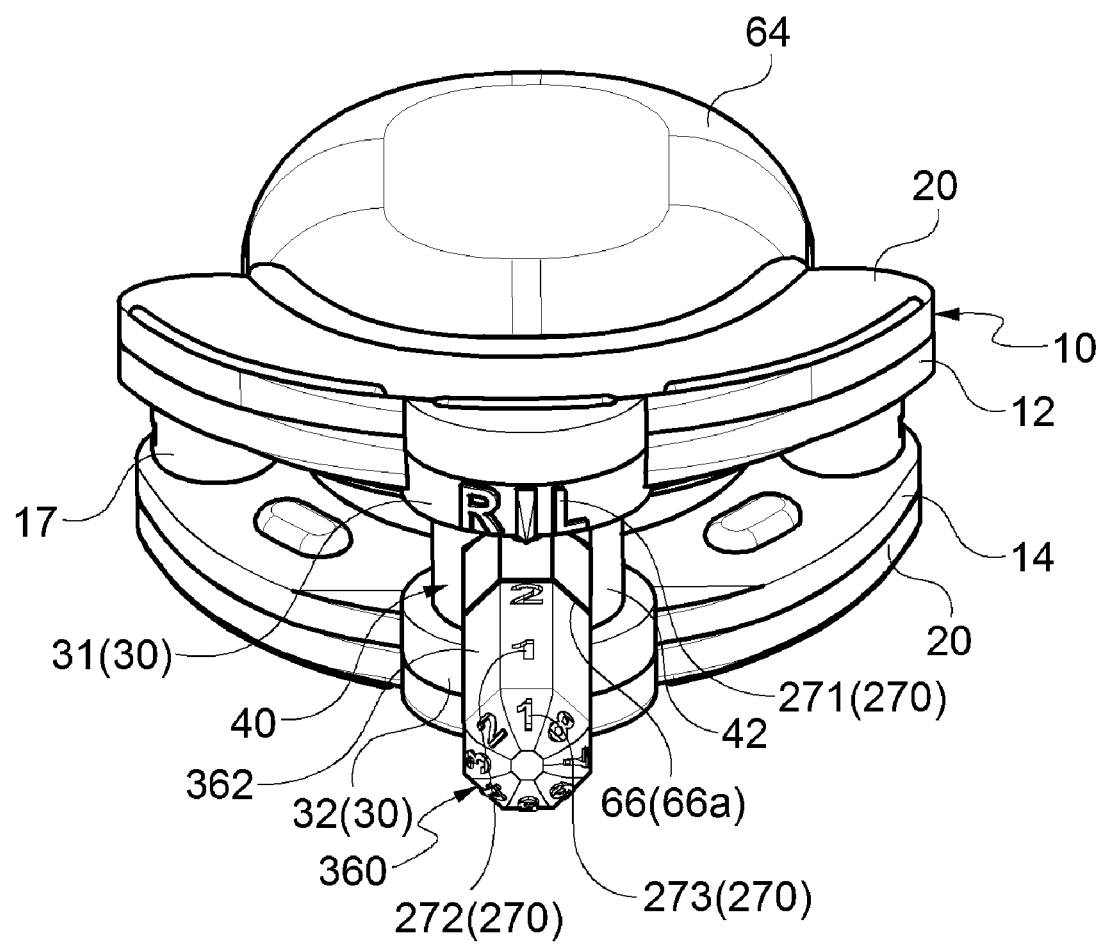
FIG. 23 is a perspective view of an oral fixation apparatus according to another embodiment of the present invention.

FIG. 23 is a perspective view of an oral fixation apparatus according to another embodiment of the present invention.

The oral fixation apparatus may include an index unit 270.

The index unit 270 may be provided in the oral fixation apparatus, thereby allowing the oral fixation apparatus to be placed in the mouth in a consistent arrangement for each individual and patient.

The index unit 270 may include a first index 271 displayed on a rotation guide 30, a second index 272 displayed on a length adjustment part 66 of a pressing unit 360, and a third index 273 displayed on a handle part 362 of the pressing unit 360.

The first index 271 may be disposed on the rotation guide 30. The first index 271 may be configured to indicate an amount that the pressing unit 360 is moved right or left in the yaw direction relative to the rotation guide 30 when it is mounted on the mounting holder 40. By storing information displayed on the first index 271, when placing the oral fixation apparatus in the mouth of the patient again, it is possible to move the pressing unit 360 by the same amount in a right or left direction in the mouth based on the stored information of the first index 271.

The second index 272 may be displayed on the length adjustment part 66 of the pressing unit 360. The insertion length of the pressing unit 360 into the mouth may be adjusted through the second index 272. That is, when placing the oral fixation apparatus in the mouth of the patient, an insertion degree of the pressing unit 360 may be determined based on the number indicated on the second index 272. By storing information including the number displayed on the second index 272, when placing the oral fixation apparatus in the mouth of the patient again, it is possible to insert the pressing unit 360 into the mouth by the same depth based on the stored number of the second index 272.

The third index 273 may be displayed on the handle part 362 of the pressing unit 360. A rotation amount of the pressing unit 360 in the roll direction relative to the mouth may be adjusted through the third index 273. That is, when placing the oral fixation apparatus in the mouth of the patient, the rotation direction and rotation amount of the pressing unit 360 relative to the roll direction may be determined based on the number indicated on the third index 273. By storing information including the number displayed on the third index 273, when placing the oral fixation apparatus in the mouth of the patient again, it is possible to rotate the pressing unit 360 so as to be the same rotated state in the roll direction in the mouth based on the stored number of the third index 273. For rotation and arrangement in the roll direction, since the handle part 362 and the mounting hole are formed in a polygonal shape corresponding to each other, the third index 273 may be displayed on each side of the handle part 362.

Data for each patient and individual on the index unit 270 may be stored in a storage unit (not illustrated). Based on the data, when repeatedly inserting the oral fixation apparatus into the mouth, it is possible to place the oral fixation apparatus in the mouth to have the same shape and the same oral state.

Hereinafter, an oral fixation apparatus according to another embodiment of the present invention will be described. In the description below, the same components or same configurations as those of the previous embodiment will not be redundantly described.

Figure 24:
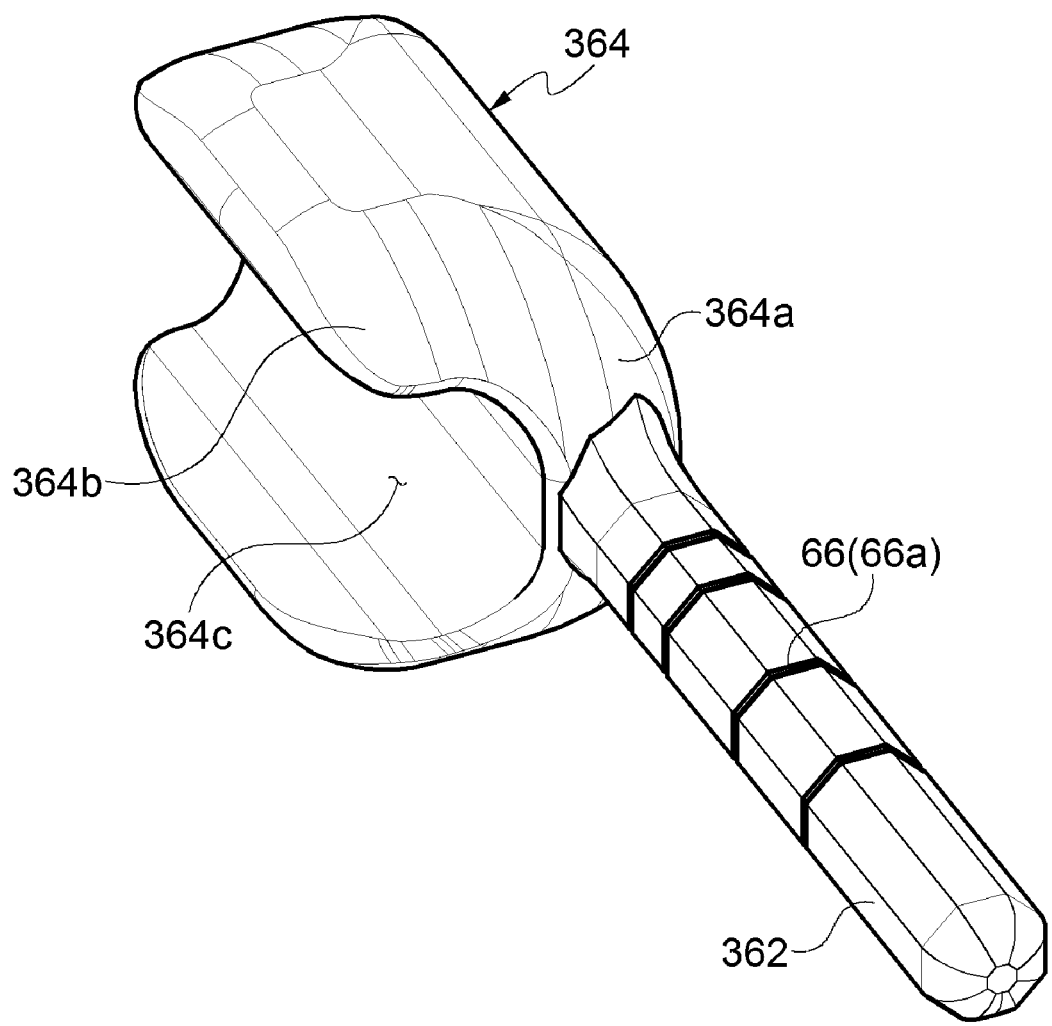
FIGS. 24 and 25 are views illustrating a pressing unit of an oral fixation apparatus according to another embodiment of the present invention.
Figure 25:
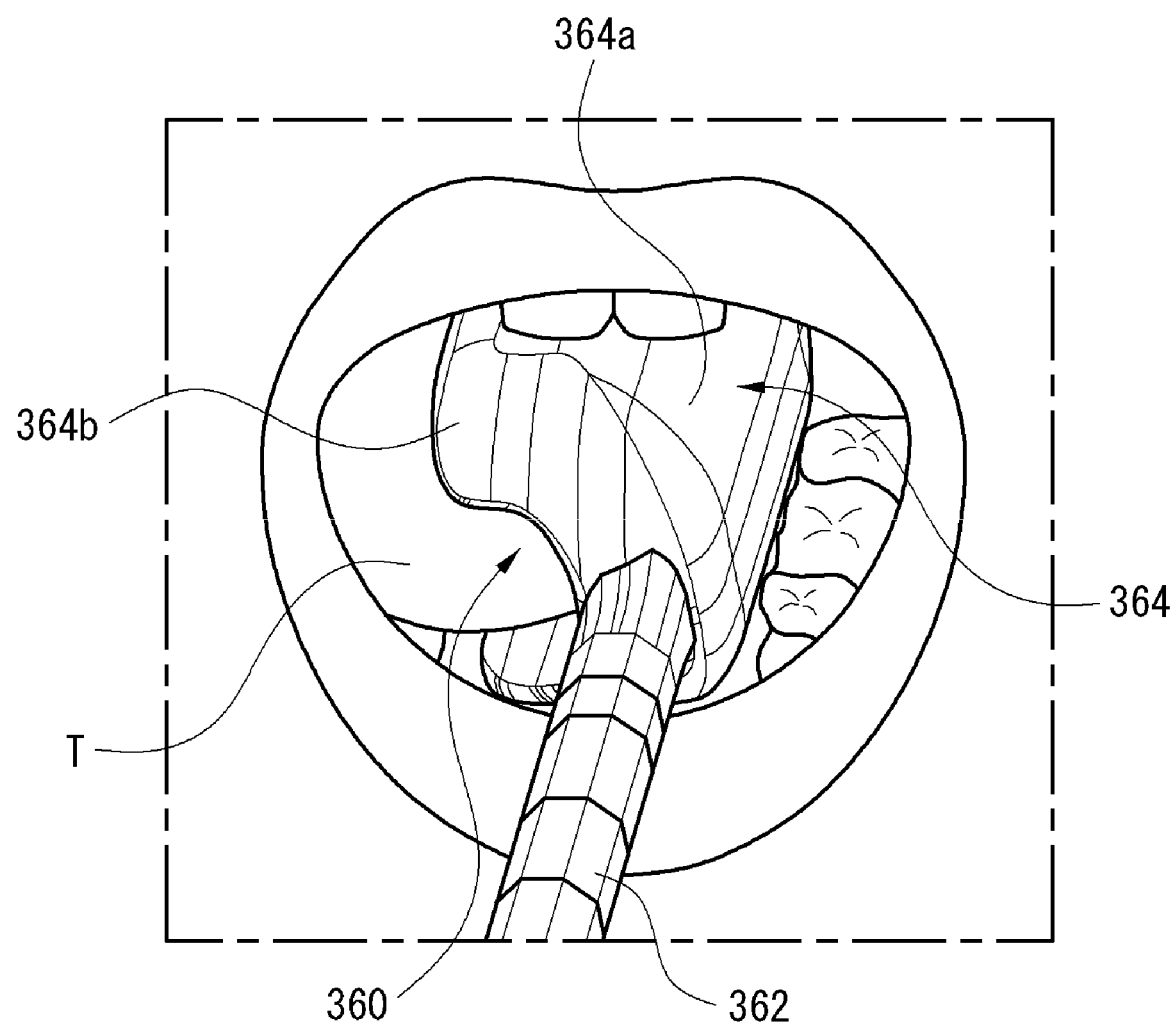

FIGS. 24 and 25 are views illustrating a pressing unit of an oral fixation apparatus according to another embodiment of the present invention.

A pressing unit 360 may include a handle part 362 and a pressing head 364.

The pressing head 364 is provided to press a tongue in the mouth. The pressing head 364 may be coupled to the handle part 362, and configured to rotate or move in conjunction with the rotation or movement of the handle part 362.

The pressing head 364 may include a head body 364a connected to the handle part 362, and an insertion guide 364b extending from the head body 364a to form a tongue insertion space 364c. The head body 364a and the insertion guide 364b may have a cross-section formed in an about U shape.

The pressing head 364 may be disposed to allow the patient's tongue to be placed in the tongue insertion space 364c. The insertion guide 364b may be configured to guide the tongue into the tongue insertion space 364c. In addition, the insertion guide 364b may be configured so that the tongue inserted into the tongue insertion space 364c is not separated from the pressing head 364. That is, a pair of insertion guides 364b may be provided so as to prevent the tongue from being separated from the tongue insertion space 364c.

As shown in FIG. 25, a tongue T inside the mouth may be guided by the insertion guide 364b to be inserted into the tongue insertion space 364c. Thereby, the pressing unit 360 may press the tongue T so as to be biased to any one side in the mouth. FIG. 25 illustrates only the pressing unit 360 of the components of the oral fixation apparatus in a figure of pressing the tongue T for the convenience of illustration and description, but of course, the oral fixation apparatus is mounted in the mouth so that the pressing unit 360 may press the tongue T.

Hereinafter, an oral fixation apparatus according to another embodiment of the present invention will be described. In the description below, the same components or same configurations as those of the previous embodiment will not be redundantly described.

Figure 26:
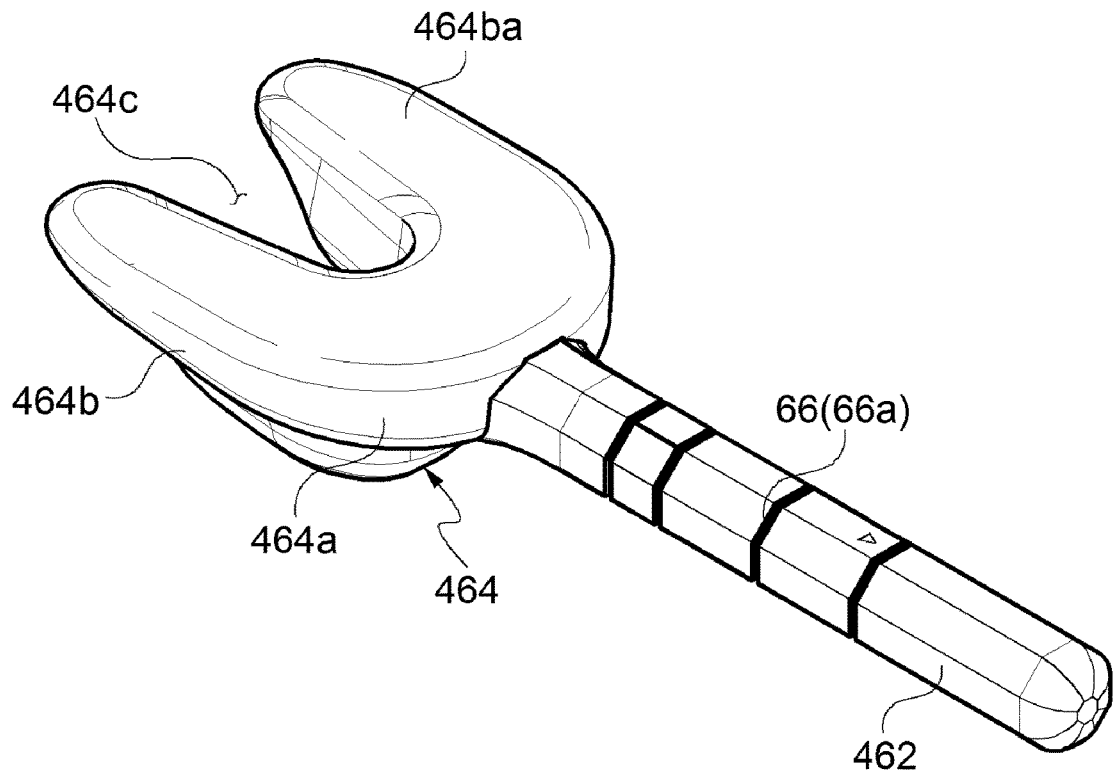
FIGS. 26, 27 and 28 are views illustrating a pressing unit of an oral fixation apparatus according to another embodiment of the present invention.
Figure 27:
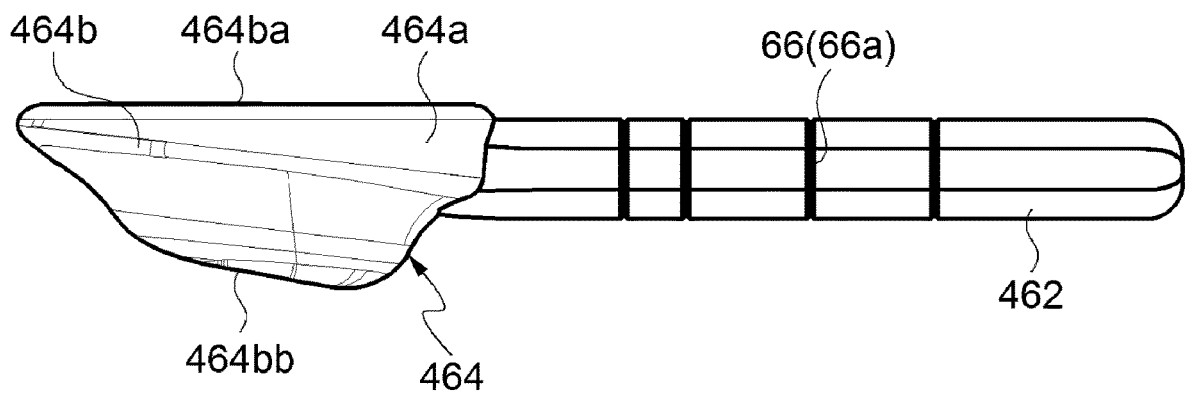
Figure 28:
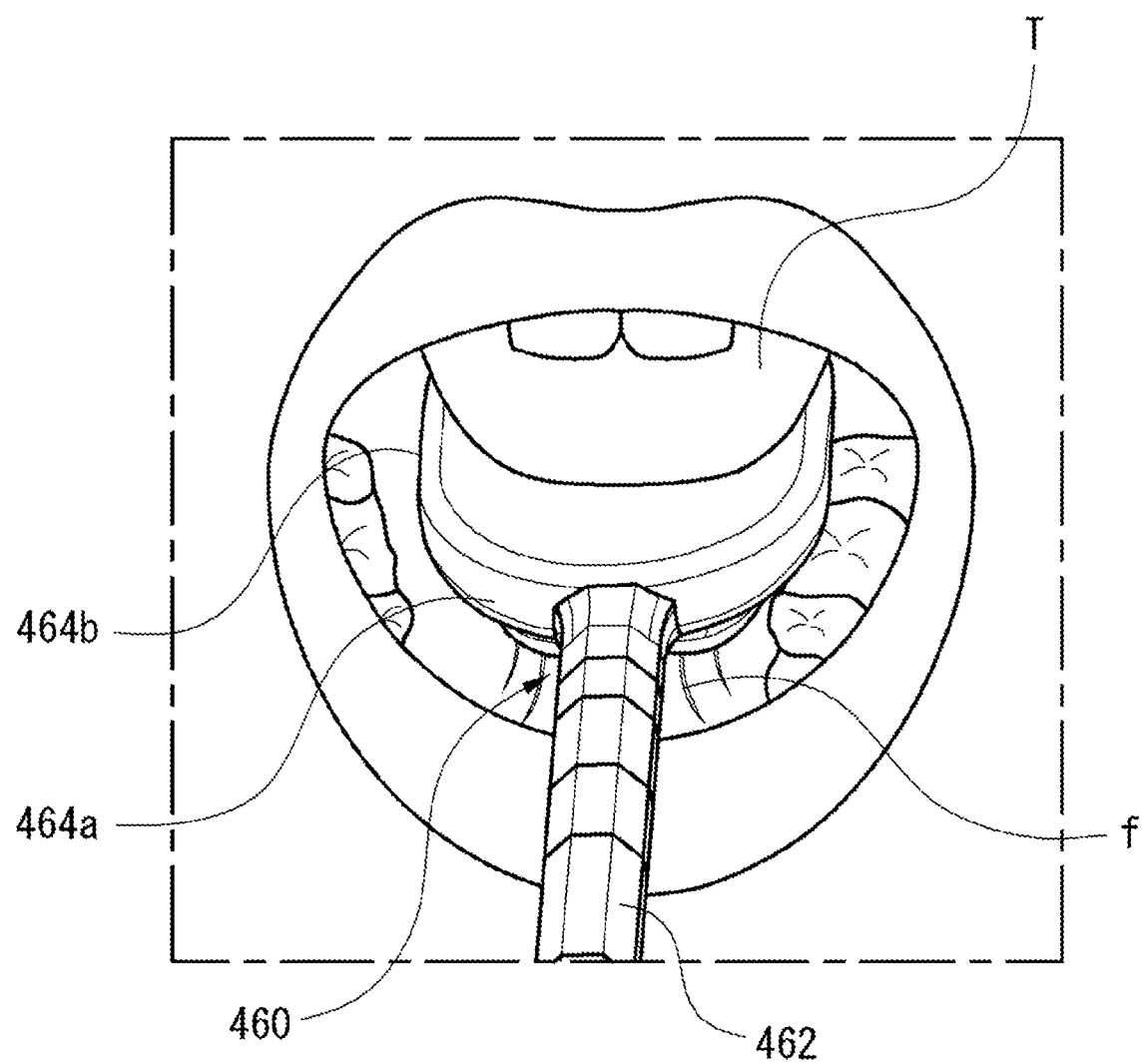

FIGS. 26, 27 and 28 are views illustrating a pressing unit of an oral fixation apparatus according to another embodiment of the present invention.

A pressing unit 460 may include a handle part 462 and a pressing head 464.

The pressing head 464 is provided to press a tongue in the mouth. The pressing head 464 may be coupled to the handle part 462, and configured to rotate or move in conjunction with the rotation or movement of the handle part 462.

The pressing head 464 may include a head body 464a connected to the handle part 462, and an insertion guide 464b extending from the head body 464a to form a frenulum linguae insertion space 464c. Specifically, a pair of insertion guides 464b are provided, and the frenulum linguae insertion space 464c may be formed therebetween. The head body 464a and the insertion guide 464b may be formed in an about U shape.

The pressing head 464 may be disposed so that the patient's frenulum linguae is placed in the frenulum linguae insertion space 464c. The insertion guide 464b may be formed by extending in the longitudinal direction so as to come into contact with an inner side of the tongue without interfering with the patient's frenulum linguae. Through this configuration, during the insertion guide 464b is inserted into a lower portion of the tongue, the patient's frenulum linguae may be placed in the frenulum linguae insertion space 464c. Thereby, it is possible to prevent the pressing unit 460 from being limited in insertion due to interfering with the frenulum linguae.

The insertion guide 464b may include a tongue seat surface 464ba for supporting a lower surface of the tongue, and a mouth seat surface 464bb for supporting a lower surface of the mouth. The tongue seat surface 464ba may be formed on an upper surface of the insertion guide 464b, and the mouth seat surface 464bb may be formed on a lower surface of the insertion guide 464b.

The tongue seat surface 464ba may be formed in a flat surface so that the lower surface of the tongue may be supported in contact therewith. Since the lower surface of the mouth forms a curved surface, the mouth seat surface 464*bb* may be formed in a curved surface so that the pressing unit 460 can be stably inserted.

As shown in FIG. 28, the frenulum linguae is inserted into the frenulum linguae insertion space 464*c*, and the lower surface of the tongue T in the mouth may be supported by the insertion guide 464*b*. Thereby, the pressing unit 460 may press the tongue so as to be biased to any one side in the mouth. In addition, the pressing unit 460 may press the tongue to face upward inside the mouth. In the present embodiment, the configuration, in which the pressing unit is rotated in the yaw direction through the rotation guide 30, has been illustrated and described, but as shown in FIGS. 26 to 28, the rotation guide may be configured so that the pressing unit is rotated in a pitch direction to lift the tongue.

FIG. 28 illustrates only the pressing unit 460 of the components of the oral fixation apparatus in a figure of pressing the tongue for the convenience of illustration and description, but of course, the oral fixation apparatus is mounted in the mouth so that the pressing unit 460 may press the tongue.

Hereinafter, an oral fixation apparatus according to another embodiment of the present invention will be described. In the description below, the same components or same configurations as those of the previous embodiment will not be redundantly described.

Figure 29:
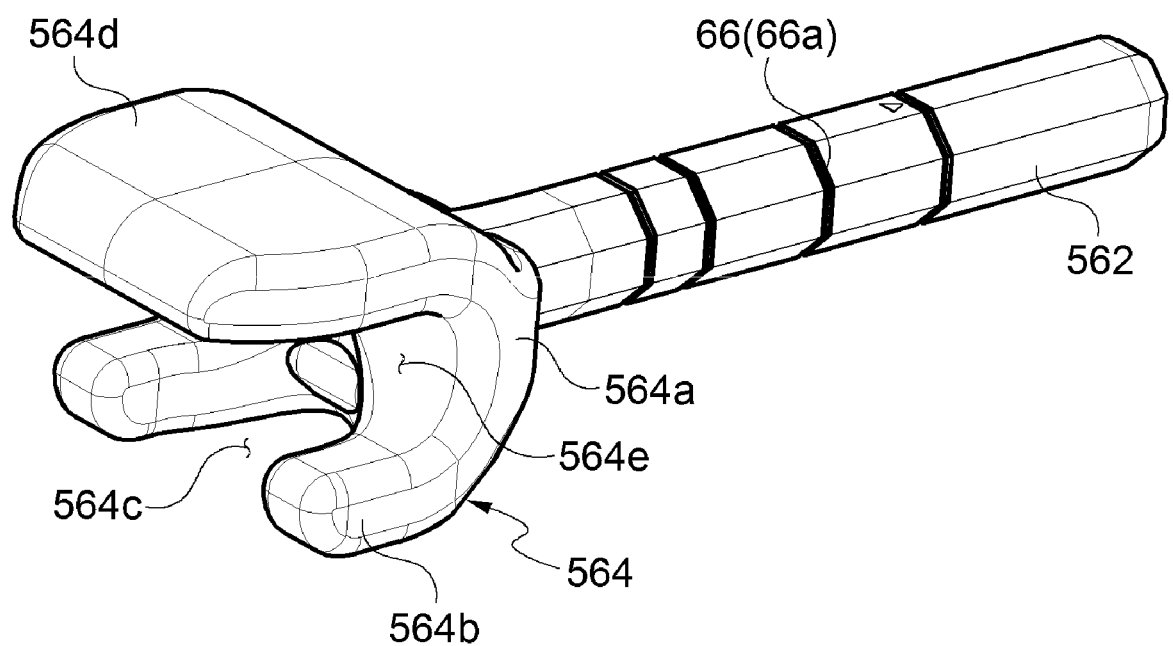
FIGS. 29, 30 and 31 are views illustrating a pressing unit of an oral fixation apparatus according to another embodiment of the present invention.
Figure 30:
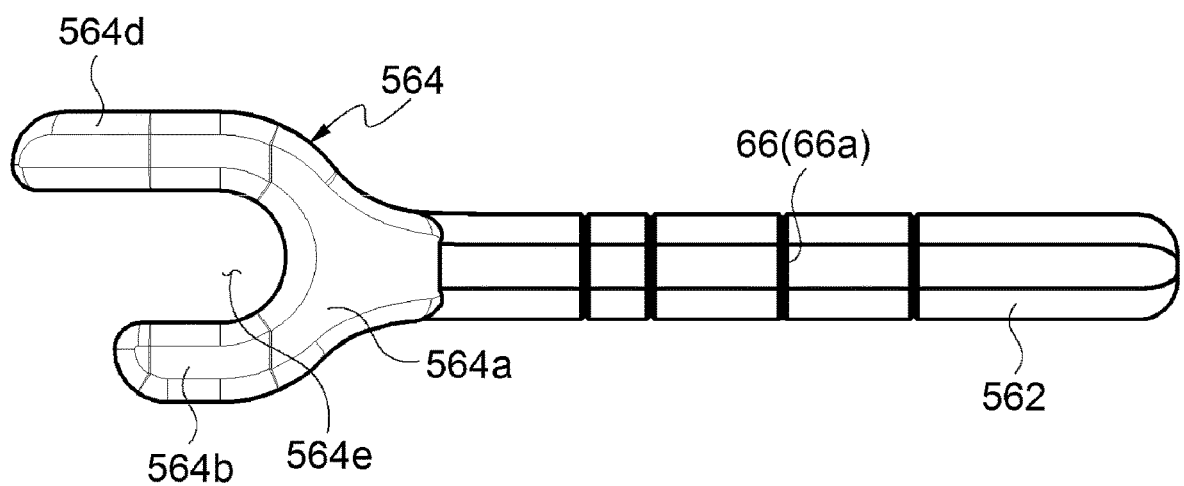
Figure 31:
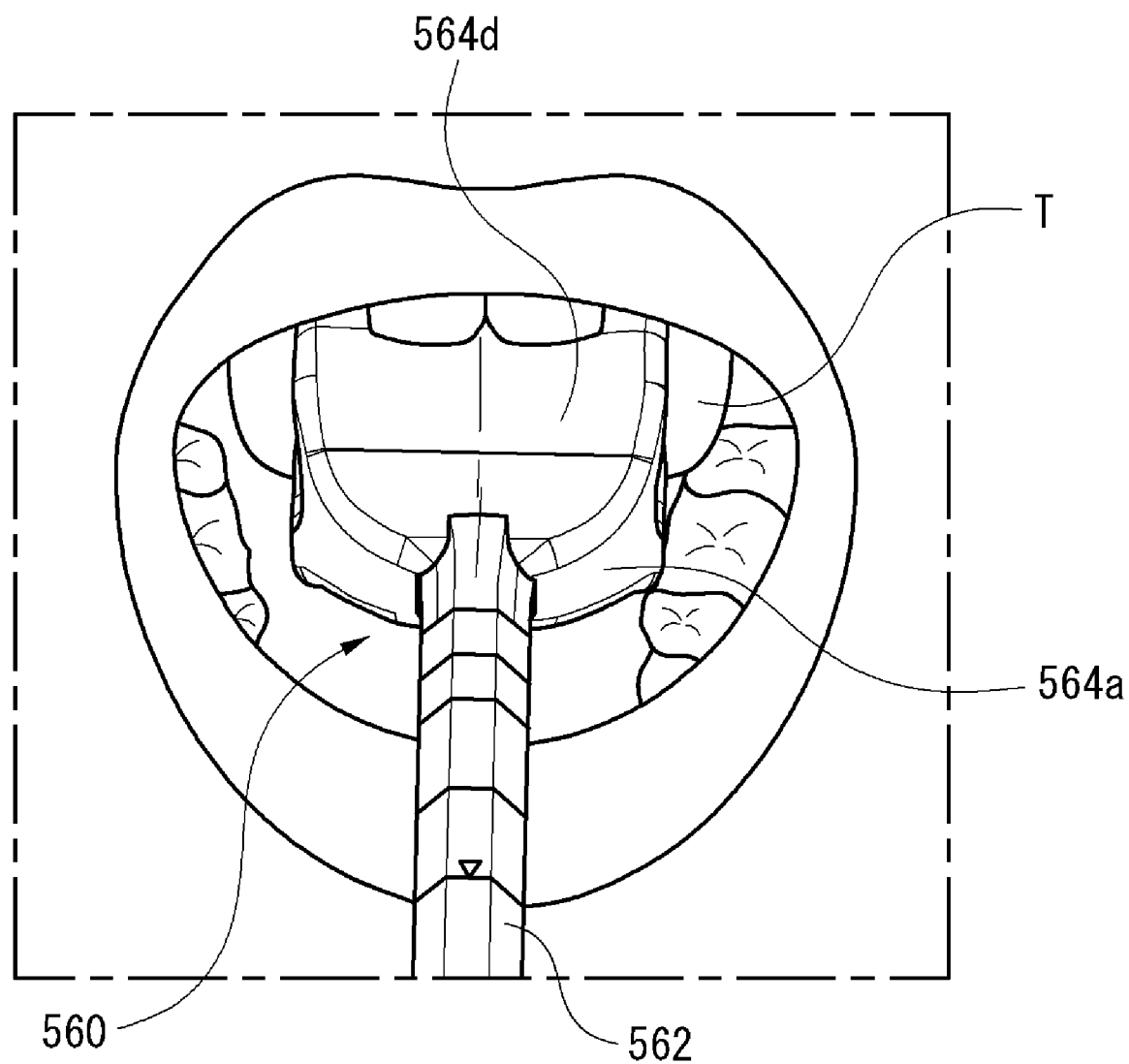

FIGS. 29, 30 and 31 are views illustrating a pressing unit of an oral fixation apparatus according to another embodiment of the present invention.

A pressing unit 560 may include a handle part 562 and a pressing head 564.

The pressing head 564 is provided to press a tongue in the mouth. The pressing head 564 may be coupled to the handle part 562, and configured to rotate or move in conjunction with the rotation or movement of the handle part 562.

The pressing head 564 may include a head body 564*a* connected to the handle part 562, and first and second insertion guides 564*b* and 564*d*.

The first insertion guides 564*b* may form a frenulum linguae insertion space 564*c*. The first insertion guides 564*b* may be formed by extending in the longitudinal direction so as to come into contact with the inner side of the tongue without interfering with the patient's frenulum linguae. During the first insertion guides 564*b* are inserted into the lower portion of the tongue, the patient's frenulum linguae may be placed in the frenulum linguae insertion space 564*c*. Thereby, it is possible to prevent the pressing unit 560 from being limited in insertion due to interfering with the frenulum linguae.

The second insertion guide 564*d* may support an upper portion of the tongue. The second insertion guide 564*d* may be disposed to be spaced apart from the first insertion guides 564*b* with a predetermined interval. Thereby, the second insertion guide 564*d* may form a tongue insertion space 564*e* together with the first insertion guides 564*b*.

Since the first and second insertion guides 564*b* and 564*d* guide the lower and upper portions of the tongue, respectively, these guides may be referred to as a lower insertion guide 564*b* and an upper insertion guide 564*d*, respectively.

As shown in FIG. 30, the pressing unit 560 may be placed in the mouth so that the frenulum linguae is inserted into the frenulum linguae insertion space 564*c* and the tongue T is inserted into the tongue insertion space 564*e*. Thereby, the pressing unit 560 may stably push the tongue to the inside of the mouth. FIG. 30 illustrates only the pressing unit 560 of the components of the oral fixation apparatus in a figure of pressing the tongue T for the convenience of illustration and description, but of course, the oral fixation apparatus is mounted in the mouth so that the pressing unit 560 may press the tongue.

Hereinafter, an oral fixation apparatus according to another embodiment of the present invention will be described. In the description below, the same components or same configurations as those of the previous embodiment will not be redundantly described.

Figure 32:
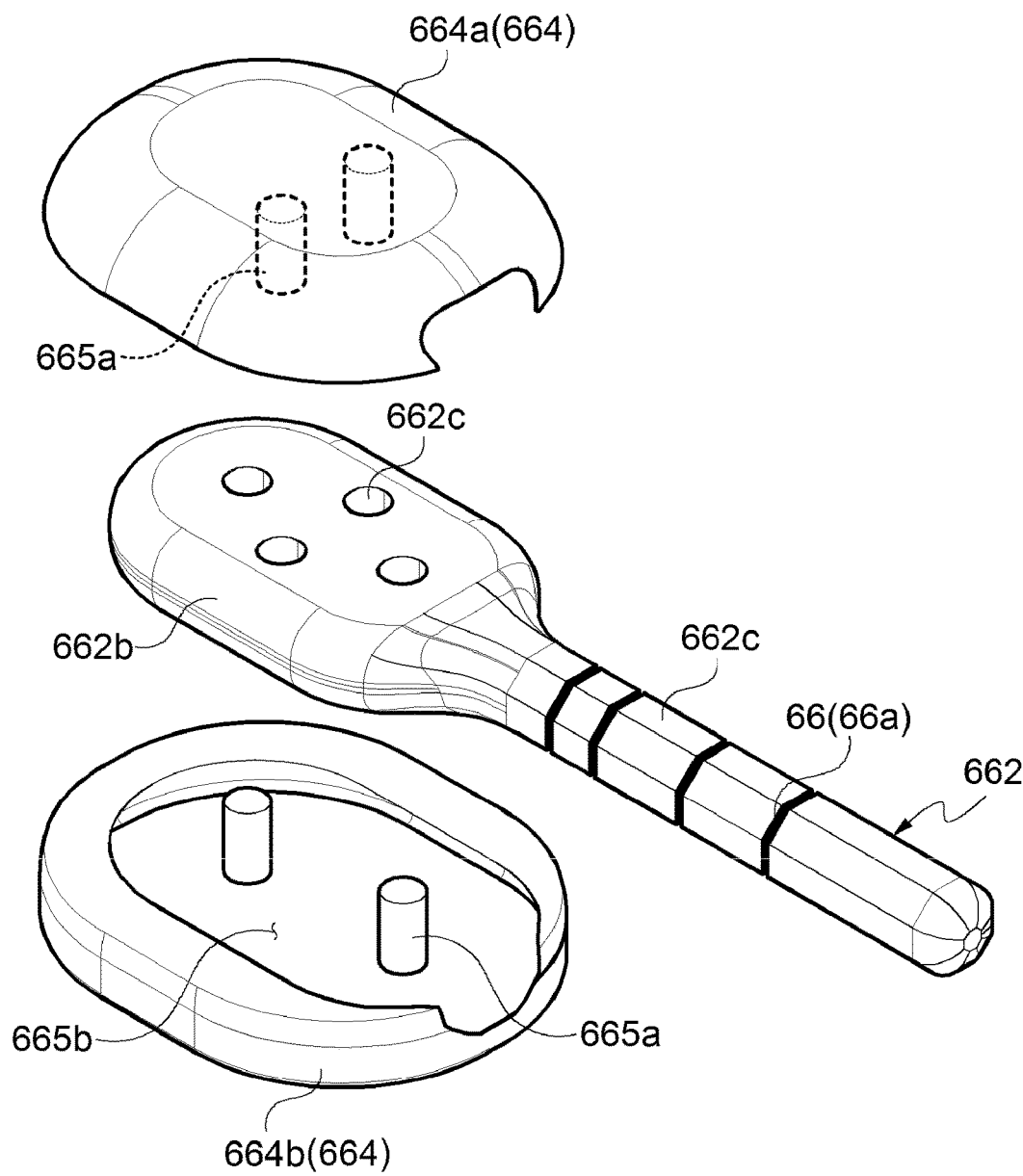
FIG. 32 is an exploded perspective view illustrating an assembly of an oral fixation apparatus according to another embodiment of the present invention.

FIG. 32 is an exploded perspective view illustrating an assembly of an oral fixation apparatus according to another embodiment of the present invention.

A pressing unit 660 may include a handle part 662 and a pressing head 664.

The pressing head 664 may be configured to be separated from the handle part 662. The handle part 662 may include a handle body 662*a* and an extension body 662*b* extending from the handle body 662*a*. The pressing head 664 may be configured to be coupled to the extension body 662*b*.

The pressing head 664 may include a first head 664*a* and a second head 664*b*.

The first and second heads 664*a* and 664*b* may be configured to be coupled to one side and the other side of the extension body 662*b*, respectively. The first and second heads 664*a* and 664*b* may include insert protrusions 665*a* formed therein, which are inserted into insertion grooves 662*c* formed in the extension body 662*b*. As the insert protrusions 665*a* are inserted into the insertion grooves 662*c*, the first and second heads 664*a* and 664*b* may be fixed to the extension body 662*b*.

The first and second heads 664*a* and 664*b* may include an arrangement space 665*b* concavely formed so that the extension body 662*b* is located therein. Thereby, the first and second heads 664*a* and 664*b* are coupled to the extension body 662*b* so that the extension body 662*b* is located in the arrangement space 665*b* inside thereof. Thus, it may be configured to prevent the extension body 662*b* from being exposed to the outside.

As such, specific embodiments of the present invention have been illustrated and described in detail. However, the present invention is not limited to the above embodiments, and it will be understood by those skilled in the art that various alterations and modifications may be implemented without departing from technical spirits of the invention described in the following claims.

What is claimed is:

1. An oral fixation apparatus comprising:
a mouthpiece configured to be mounted in a mouth; and
a pressing unit movably coupled to the mouthpiece, the pressing unit configured to press a tongue in the mouth and moves between a first position and a second position in which the pressing unit is rotated in a yaw direction from the first position;
the pressing unit comprises:
a handle part; and
a pressing head located at an end of the handle part, and configured to be in contact with the tongue so as to press the tongue by a rotation in the yaw direction, and
the oral fixation apparatus further comprises
a rotation guide forming a rotation axis of the pressing unit in the yaw direction, wherein the rotation guide maintains the pressing unit located in either the first position or the second position;
a length adjustment part configured to adjust a length in which the pressing head is inserted into the mouth, wherein the length adjustment part has a plurality of adjustment grooves into which an insert protrusion located on the mouthpiece is selectively inserted, which are spaced apart from each other in a longitudinal direction of the handle part; and an index unit configured to indicate a position of the pressing unit, the index unit comprising:
a first index disposed on the rotation guide to indicate a rotation direction and a rotation amount of the pressing unit in the yaw direction thereof;
a second index disposed on the length adjustment part to indicate an insertion degree of the pressing unit; and
a third index disposed on the handle part to indicate a rotation direction and a rotation amount of the pressing unit in the roll direction thereof.

2. The oral fixation apparatus according to claim 1, further comprising a mounting holder which has a mounting hole in which the pressing unit is mounted, and rotates on the rotation axis relative to the rotation guide together with the pressing unit,
wherein the mounting holder and the rotation guide maintain the pressing unit located in either the first position or the second position.

3. The oral fixation apparatus according to claim 2, wherein the mounting holder comprises tooth-shaped engaging gears formed on an outer surface thereof, and
the rotation guide comprises gear grooves formed in an inner surface thereof and configured to be engaged with the engaging gears so as to limit a rotation of the mounting holder.

4. The oral fixation apparatus according to claim 3, wherein the engaging gears comprise:
an adjustment gear composed of teeth formed with a longer length than a protruding length of adjacent teeth; and
the gear grooves comprise a plurality of adjustment grooves formed with a deeper depth than a depth of adjacent grooves, wherein the plurality of adjustment grooves are configured so that the adjustment gear is inserted into any one adjustment groove of the plurality of adjustment grooves.

5. The oral fixation apparatus according to claim 2, wherein a position of the pressing unit is changed between a first state and a second state in which the pressing unit is rotated in a roll direction from the first state; and
the position of the pressing unit is changed by separating and mounting the pressing unit from and in the mounting holder.

6. The oral fixation apparatus according to claim 5, wherein the mounting hole has a cross section formed in a polygonal shape corresponding to an outer surface of the pressing unit so as to limit a rotation of the pressing unit in the roll direction with being mounted in the mounting hole.

7. The oral fixation apparatus according to claim 2, wherein the mouthpiece comprises a first body corresponding to upper teeth and a second body corresponding to lower teeth; and
the rotation guide comprises:
a first guide part disposed in the first body to guide a rotation of the mounting holder on one side; and
a second guide part disposed in the second body to guide the rotation of the mounting holder on another side.

8. The oral fixation apparatus according to claim 7, wherein the first and second bodies are symmetrically arranged; and
a guide part of the first and second guide parts is disposed to protrude forward from the first and second bodies so as to have an asymmetric structure relative to the symmetric first and second bodies.

9. The oral fixation apparatus according to claim 1, wherein the mouthpiece comprises:
a first body configured to correspond to upper teeth and a second body configured to correspond to lower teeth; and
a shape holding part disposed on an upper portion of the first body and a lower portion of the second body, respectively, wherein a reference groove is formed while the upper and lower teeth are inserted therein.

10. The oral fixation apparatus according to claim 9, wherein the shape holding part is configured to be cured in a state in which the reference groove is formed.

11. The oral fixation apparatus according to claim 9, wherein the shape holding part comprises:
inclined surfaces slantly formed on a surface thereof; and
a seat surface formed on the surface of the shape holding part, wherein the seat surface and the inclined surfaces form an insertion space which is concave on the surface of the shape holding part, wherein the reference groove is disposed on the seat surface.

12. The oral fixation apparatus according to claim 9, wherein the mouthpiece further comprises:
first and second guide bodies disposed between the shape holding part and the first and second bodies, wherein the first and second guide bodies are detachably coupled to the first and second bodies together with the shape holding part mounted on one surface thereof.

13. The oral fixation apparatus according to claim 9, wherein the pressing unit moves relative to the mouthpiece between the first and second bodies.

14. The oral fixation apparatus according to claim 1, wherein the handle part is configured to be exposed to an outside of the mouth when the oral fixation apparatus is mounted in the mouth.

15. The oral fixation apparatus according to claim 1, wherein the pressing unit comprises:
a handle part; and
a pressing head located at an end of the handle part, and configured to be in contact with the tongue, the pressing head comprising:
a head body; and
a pair of insertion guides extending from the head body, wherein the pair of insertion guides form a tongue insertion space therebetween configured for the tongue to be inserted therein.

16. The oral fixation apparatus according to claim 1, wherein the pressing unit comprises:
a handle part; and
a pressing head located at an end of the handle part, and configured to be in contact with the tongue, the pressing head comprising:
a head body;
a pair of first insertion guides extending from the head body, wherein the pair of first insertion guides form a frenulum linguae insertion space therebetween configured for a frenulum linguae to be placed therein; and
a second insertion guide disposed to be spaced apart from the pair of first insertion guides, wherein the second insertion guide forms a tongue insertion space between the same and the pair of first insertion guides.

17. The oral fixation apparatus according to claim 1, wherein the pressing unit comprises:
a handle part; and a pressing head located at an end of the handle part, and configured to be in contact with the tongue, the pressing head comprising:
 a head body; and
 a pair of insertion guides extending from the head body, wherein the pair of insertion guides form a frenulum linguae insertion space therebetween configured for a frenulum linguae to be placed therein.

\* \* \* \* \*